(12) United States Patent
Frank

(10) Patent No.: US 10,577,575 B2
(45) Date of Patent: *Mar. 3, 2020

(54) COATING A BIOREACTOR

(71) Applicant: Terumo BCT, Inc., Lakewood, CO (US)

(72) Inventor: Nathan D. Frank, Arvada, CO (US)

(73) Assignee: Terumo BCT, Inc., Lakewood, CO (US)

( * ) Notice: Subject to any disclaimer, the term of this patent is extended or adjusted under 35 U.S.C. 154(b) by 307 days.

This patent is subject to a terminal disclaimer.

(21) Appl. No.: 15/616,745

(22) Filed: Jun. 7, 2017

(65) Prior Publication Data
US 2017/0349872 A1    Dec. 7, 2017

Related U.S. Application Data

(60) Provisional application No. 62/347,012, filed on Jun. 7, 2016.

(51) Int. Cl.
C12M 1/00    (2006.01)
C12M 1/34    (2006.01)
C12M 1/36    (2006.01)
C12M 1/12    (2006.01)

(52) U.S. Cl.
CPC ............ *C12M 23/20* (2013.01); *C12M 23/50* (2013.01); *C12M 25/00* (2013.01); *C12M 29/16* (2013.01); *C12M 41/00* (2013.01); *C12M 41/48* (2013.01)

(58) Field of Classification Search
CPC ...... C12M 23/20; C12M 23/50; C12M 25/00; C12M 29/16; C12M 41/00; C12M 41/48
See application file for complete search history.

(56) References Cited

U.S. PATENT DOCUMENTS

2015/0140653 A1*  5/2015  Jones ..................... C12M 23/50
                                                              435/366

* cited by examiner

*Primary Examiner* — Shamim Ahmed
*Assistant Examiner* — Bradford M Gates
(74) *Attorney, Agent, or Firm* — Terumo BCT, Inc. IP Law Department

(57) ABSTRACT

Embodiments for coating a bioreactor with a reagent are described. The embodiments may provide for changing flow rates, direction of flow, and/or bioreactor rotation to enhance the coating of the bioreactor prior to growing cells in the bioreactor.

25 Claims, 22 Drawing Sheets

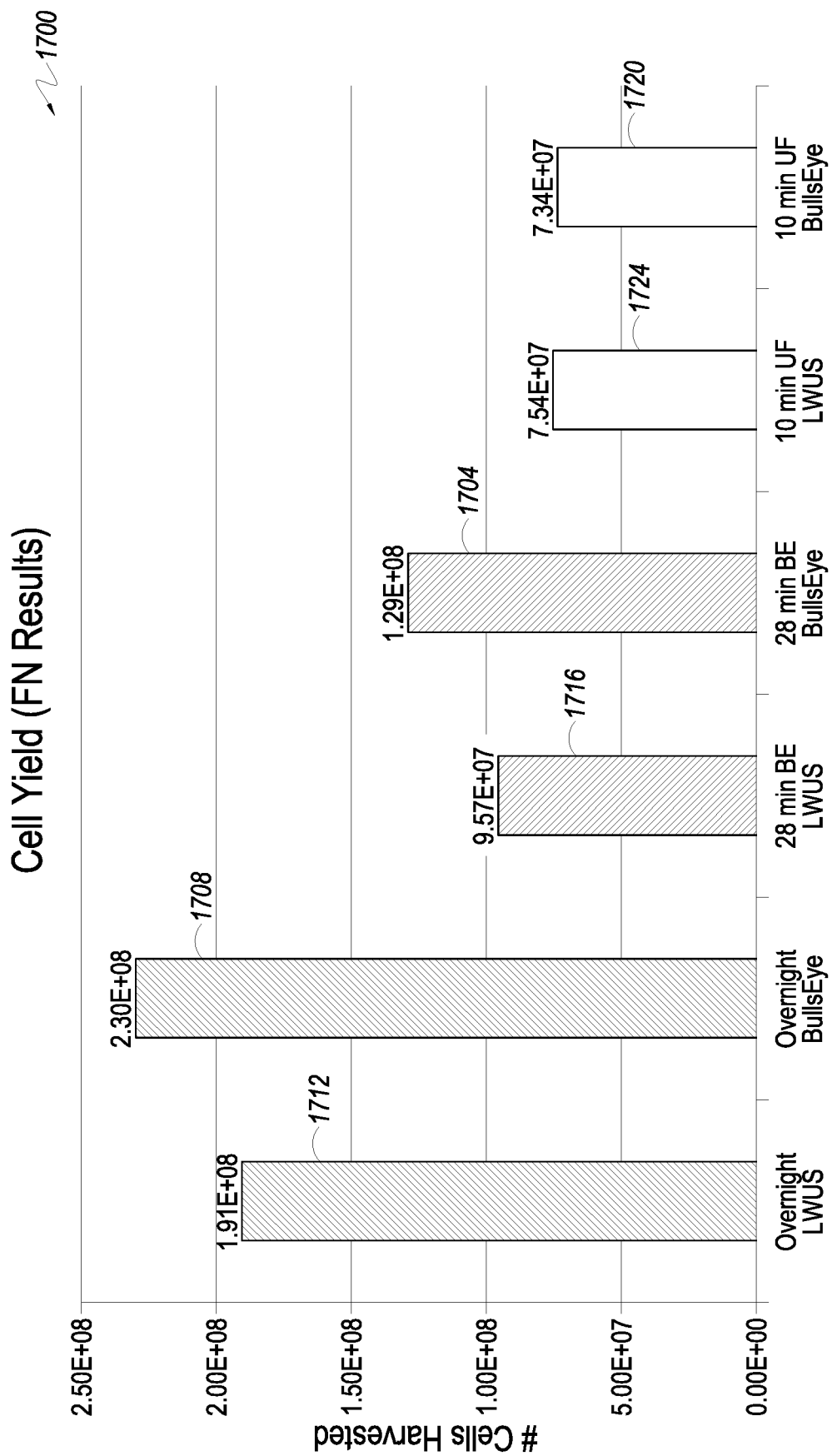

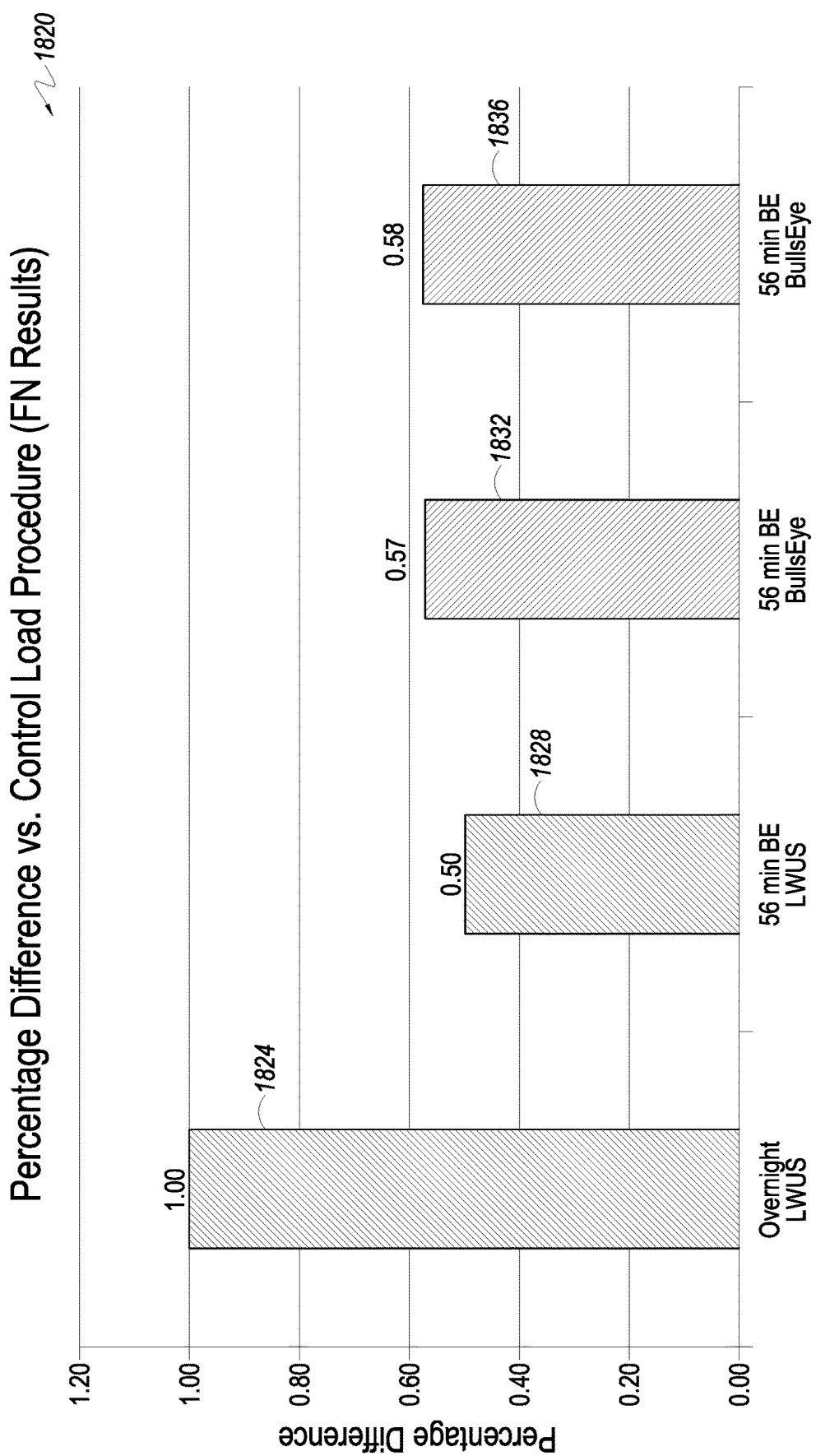

COATING A BIOREACTOR

CROSS-REFERENCE TO RELATED APPLICATION(S)

This patent application claims priority to U.S. Provisional Patent Application No. 62/347,012, entitled "COATING A BIOREACTOR," filed Jun. 7, 2016 and hereby incorporated by reference in its entirety as if set forth herein in full.

BACKGROUND

Cell Expansion Systems (CESs) may be used to expand and differentiate a variety of cell types that may be used for both research and therapeutic purposes. Cells, depending on their type, may grow under different conditions. For example, some cells may grow by first attaching to a surface of a bioreactor, e.g., adherent cells. The materials used in constructing a bioreactor may not have the properties that allow cells to attach to surfaces of the bioreactor. Therefore, in order to promote the attachment of cells to surfaces of the bioreactor, the bioreactor may be coated with a reagent that promotes attachment of the cells.

Embodiments have been made in light of these and other considerations. However, the relatively specific problems discussed above do not limit the applicability of the embodiments of the present disclosure.

SUMMARY

The summary is provided to introduce aspects of some embodiments in a simplified form, and is not intended to identify key or essential elements, nor is it intended to limit the scope of the claims.

Embodiments provide for coating a bioreactor with a reagent. The embodiments may provide for changing flow rate speeds, direction of flow, and/or rotating the bioreactor to enhance the coating of the bioreactor with the reagent prior to growing cells in the bioreactor.

Embodiments may include circulating a first fluid at a first flow rate through a bioreactor of a cell expansion system, the first fluid including a reagent. During the circulating, the bioreactor may be maintained in a first orientation (e.g., horizontal orientation) for a first predetermined period of time to allow at least a first portion of the reagent to coat the bioreactor.

After the first predetermined period of time, the first fluid may be circulated at a second flow rate (slower than the first flow rate) through the bioreactor for a second period of time to allow a second portion of the reagent to coat the bioreactor. In embodiments, the fluid may be circulated in an opposite direction than the circulation of the first step. In embodiments, after the second period of time, the first fluid may be circulated at a third flow rate (slower than the second flow rate) through the bioreactor for a third period of time to allow a fourth portion of the reagent to coat the bioreactor. In some embodiments, the fluid may be circulated in an opposite direction than the circulation of the second step (e.g., in the same direction of the first step). In other embodiments, the fluid may be circulated in the same direction as the circulation of the second step (e.g., in the opposite direction of the first step). A second fluid may then be circulated through the bioreactor to remove a third portion of the reagent from the bioreactor, e.g., a portion of the reagent that has not coated a surface of the bioreactor.

BRIEF DESCRIPTION OF THE DRAWINGS

Non-limiting and non-exhaustive embodiments are described with reference to the following figures.

FIG. 17A illustrates example results of expanding cells using various coating and cell loading procedures in accordance with embodiments.

FIG. 18B depicts example results of expanding cells using various coating and cell loading procedures in accordance with embodiments.

DETAILED DESCRIPTION

Figure 1A:
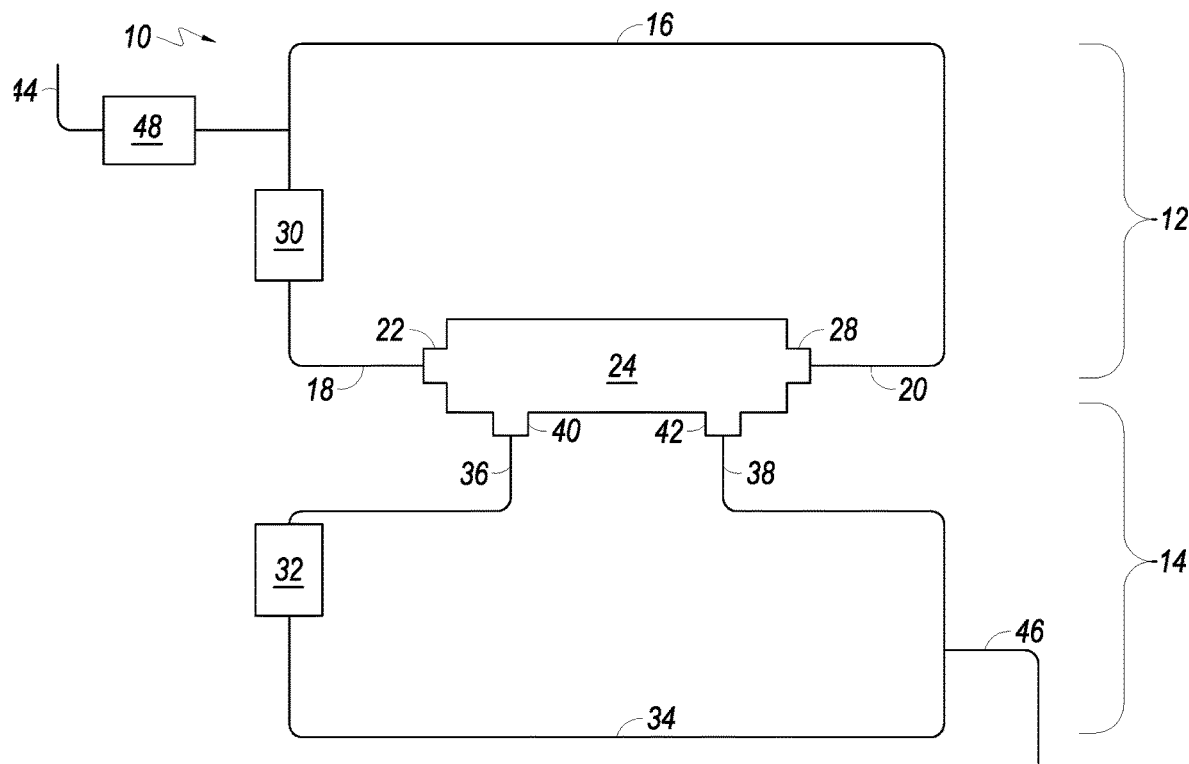
FIG. 1A depicts an embodiment of a cell expansion system (CES).

The principles of the present disclosure may be further understood by reference to the following detailed description and the embodiments depicted in the accompanying drawings. It should be understood that although specific features are shown and described below with respect to detailed embodiments, the present disclosure is not limited to the embodiments described below.

Reference will now be made in detail to the embodiments illustrated in the accompanying drawings and described below. Wherever possible, the same reference numerals are used in the drawings and the description to refer to the same or like parts.

A schematic of an example cell expansion system (CES) is depicted in FIG. 1A, in accordance with embodiments of the present disclosure. CES 10 includes first fluid circulation path 12 and second fluid circulation path 14. First fluid flow path 16 has at least opposing ends 18 and 20 fluidly associated with a hollow fiber cell growth chamber 24 (also referred to herein as a "bioreactor"), according to embodiments. Specifically, opposing end 18 may be fluidly associated with a first inlet 22 of cell growth chamber 24, and opposing end 20 may be fluidly associated with first outlet 28 of cell growth chamber 24. Fluid in first circulation path 12 flows through the interior of hollow fibers 116 (see FIG. 1B) of hollow fiber membrane 117 (see FIG. 1B) disposed in cell growth chamber 24 (cell growth chambers and hollow fiber membranes are described in more detail infra). Further, first fluid flow control device 30 may be operably connected to first fluid flow path 16 and may control the flow of fluid in first circulation path 12.

Second fluid circulation path 14 includes second fluid flow path 34, cell growth chamber 24, and a second fluid flow control device 32. The second fluid flow path 34 has at least opposing ends 36 and 38, according to embodiments. Opposing ends 36 and 38 of second fluid flow path 34 may be fluidly associated with inlet port 40 and outlet port 42 respectively of cell growth chamber 24. Fluid flowing through cell growth chamber 24 may be in contact with the outside of hollow fiber membrane 117 (see FIG. 1B) in the cell growth chamber 24, in which a hollow fiber membrane comprises a plurality of hollow fibers. Second fluid circulation path 14 may be operably connected to second fluid flow control device 32.

Figure 1B:
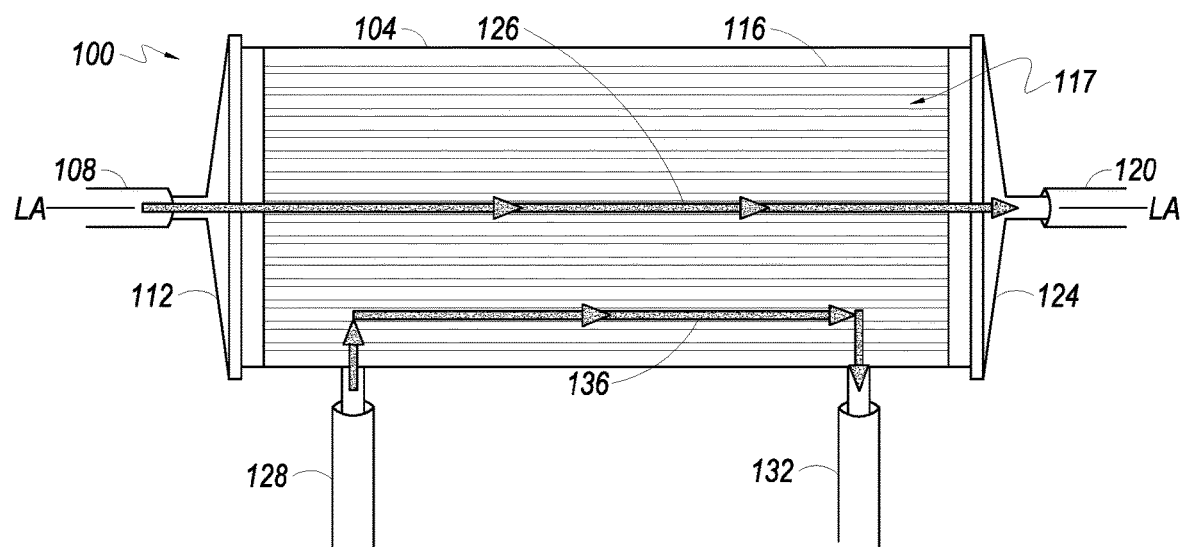
FIG. 1B illustrates a front elevation view of an embodiment of a bioreactor showing circulation paths through the bioreactor.

First and second fluid circulation paths 12 and 14 may thus be separated in cell growth chamber 24 by a hollow fiber membrane 117 (see FIG. 1B). Fluid in first fluid circulation path 12 flows through the intracapillary ("IC") space of the hollow fibers in the cell growth chamber 24. First circulation path 12 may be referred to as the "IC loop." Fluid in second circulation path 14 flows through the extracapillary ("EC") space in the cell growth chamber 24. Second fluid circulation path 14 may be referred to as the "EC loop." Fluid in first fluid circulation path 12 may flow in either a co-current or counter-current direction with respect to flow of fluid in second fluid circulation path 14, according to embodiments.

Fluid inlet path 44 may be fluidly associated with first fluid circulation path 12. Fluid inlet path 44 allows fluid into first fluid circulation path 12, while fluid outlet path 46 allows fluid to leave CES 10. Third fluid flow control device 48 may be operably associated with fluid inlet path 44. Alternatively, third fluid flow control device 48 may alternatively be associated with first outlet path 46.

Fluid flow control devices as used herein may comprise a pump, valve, clamp, or combination thereof, according to embodiments. Multiple pumps, valves, and clamps can be arranged in any combination. In various embodiments, the fluid flow control device is or includes a peristaltic pump. In embodiments, fluid circulation paths, inlet ports, and outlet ports may be constructed of tubing of any material.

Various components are referred to herein as "operably associated." As used herein, "operably associated" refers to components that are linked together in operable fashion and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g., a peristaltic pump that pumps fluids through flexible tubing by compressing the exterior of the tube).

Generally, any kind of fluid, including buffers, protein containing fluid, and cell-containing fluid, for example, can flow through the various circulations paths, inlet paths, and outlet paths. As used herein, "fluid," "media," and "fluid media" are used interchangeably.

Turning to FIG. 1B, an example of a hollow fiber cell growth chamber 100 which may be used with the present disclosure is shown in front side elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132.

According to embodiments of the present disclosure, fluid in a first circulation path enters cell growth chamber 100 through IC inlet port 108 at a first longitudinal end 112 of the cell growth chamber 100, passes into and through the intracapillary side (referred to in various embodiments as the intracapillary ("IC") side or "IC space" of a hollow fiber membrane) of a plurality of hollow fibers 116 comprising hollow fiber membrane 117, and out of cell growth chamber 100 through IC outlet port 120 located at a second longitudinal end 124 of the cell growth chamber 100. The fluid path between the IC inlet port 108 and the IC outlet port 120 defines the IC portion 126 of the cell growth chamber 100. Fluid in a second circulation path flows in the cell growth chamber 100 through EC inlet port 128, comes in contact with the extracapillary side or outside (referred to as the "EC side" or "EC space" of the membrane) of the hollow fibers 116, and exits cell growth chamber 100 via EC outlet port 132. The fluid path between the EC inlet port 128 and the EC outlet port 132 comprises the EC portion 136 of the cell growth chamber 100. Fluid entering cell growth chamber 100 via the EC inlet port 128 may be in contact with the outside of the hollow fibers 116. Small molecules (e.g., ions, water, oxygen, lactate, etc.) may diffuse through the hollow fibers 116 from the interior or IC space of the hollow fiber to the exterior or EC space, or from the EC space to the IC space. Large molecular weight molecules, such as growth factors, are typically too large to pass through the hollow fiber membrane, and may remain in the IC space of the hollow fibers 116. The media may be replaced as needed, in embodiments. Media may also be circulated through an oxygenator or gas transfer module to exchange gasses as needed. Cells may be contained within a first circulation path and/or a second circulation path, as described below, and may be on either the IC side and/or EC side of the membrane, according to embodiments.

The material used to make the hollow fiber membrane 117 may be any biocompatible polymeric material which is capable of being made into hollow fibers. One material which may be used is a synthetic polysulfone-based material, according to an embodiment of the present disclosure. In order for the cells to adhere to the surface of the hollow fibers, the surface may be modified in some way, either by coating at least the cell growth surface with a protein such as fibronectin or collagen, for example, or by exposing the surface to radiation, according to embodiments. Gamma treating the membrane surface allows for attachment of adherent cells without additionally coating the membrane with fibronectin, cryoprecipitate, or the like. Bioreactors made of gamma treated membranes may be reused. Other coatings and/or treatments for cell attachment may be used in accordance with embodiments of the present disclosure.

Figure 1C:
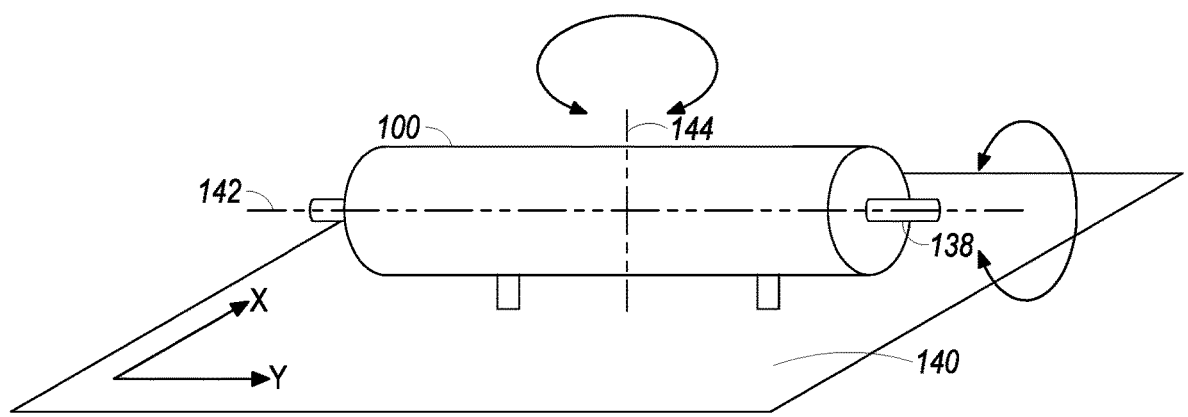
FIG. 1C depicts a rocking device for moving a cell growth chamber rotationally or laterally during operation of a cell expansion system, according to embodiments of the present disclosure.

In embodiments, the CES (such as CES 500 (see FIG. 5) and/or CES 600 (see FIG. 6), for example) may include a device configured to move or "rock" the cell growth chamber relative to other components of the cell expansion system by attaching it to a rotational and/or lateral rocking device. FIG. 1C shows one such device, in which a bioreactor 100 may be rotationally connected to two rotational rocking components and to a lateral rocking component, according to an embodiment.

A first rotational rocking component 138 rotates the bioreactor 100 around central axis 142 of the bioreactor 100. Rotational rocking component 138 may be rotationally associated with bioreactor 100. In embodiments, bioreactor 100 may be rotated continuously in a single direction around central axis 142 in a clockwise or counterclockwise direction. Alternatively, bioreactor 100 may rotate in alternating fashion, first clockwise, then counterclockwise, for example, around central axis 142, according to embodiments.

The CES may also include a second rotational rocking component that rotates bioreactor 100 around rotational axis 144. Rotational axis 144 may pass through the center point of bioreactor 100 and may be normal to central axis 142. Bioreactor 100 may be rotated continuously in a single direction around rotational axis 144 in a clockwise or counterclockwise direction, in embodiments. Alternatively, bioreactor 100 may be rotated around rotational axis 144 in an alternating fashion, first clockwise, then counterclockwise, for example. In various embodiments, bioreactor 100 may also be rotated around rotational axis 144 and positioned in a horizontal or vertical orientation relative to gravity.

In embodiments, lateral rocking component 140 may be laterally associated with bioreactor 100. The plane of lateral rocking component 140 moves laterally in the −x and −y directions, in embodiments. The settling of cells in the bioreactor may be reduced by movement of cell-containing media within the hollow fibers, according to embodiments.

The rotational and/or lateral movement of a rocking device may reduce the settling of cells within the device and reduce the likelihood of cells becoming trapped within a portion of the bioreactor. The rate of cells settling in the cell growth chamber is proportional to the density difference between the cells and the suspension media, according to Stoke's Law. In some embodiments, a 180 degree rotation (fast) with a pause (having a total combined time of 30 seconds, for example) repeated as described above keeps non-adherent red blood cells suspended. A minimum rotation of about 180 degrees would be preferred in an embodiment; however, one could use rotation of up to 360 degrees or greater. Different rocking components may be used separately, or may be combined in any combination. For example, a rocking component that rotates bioreactor 100 around central axis 142 may be combined with the rocking component that rotates bioreactor 100 around axis 144. Likewise, clockwise and counterclockwise rotation around different axes may be performed independently in any combination.

Figure 2:
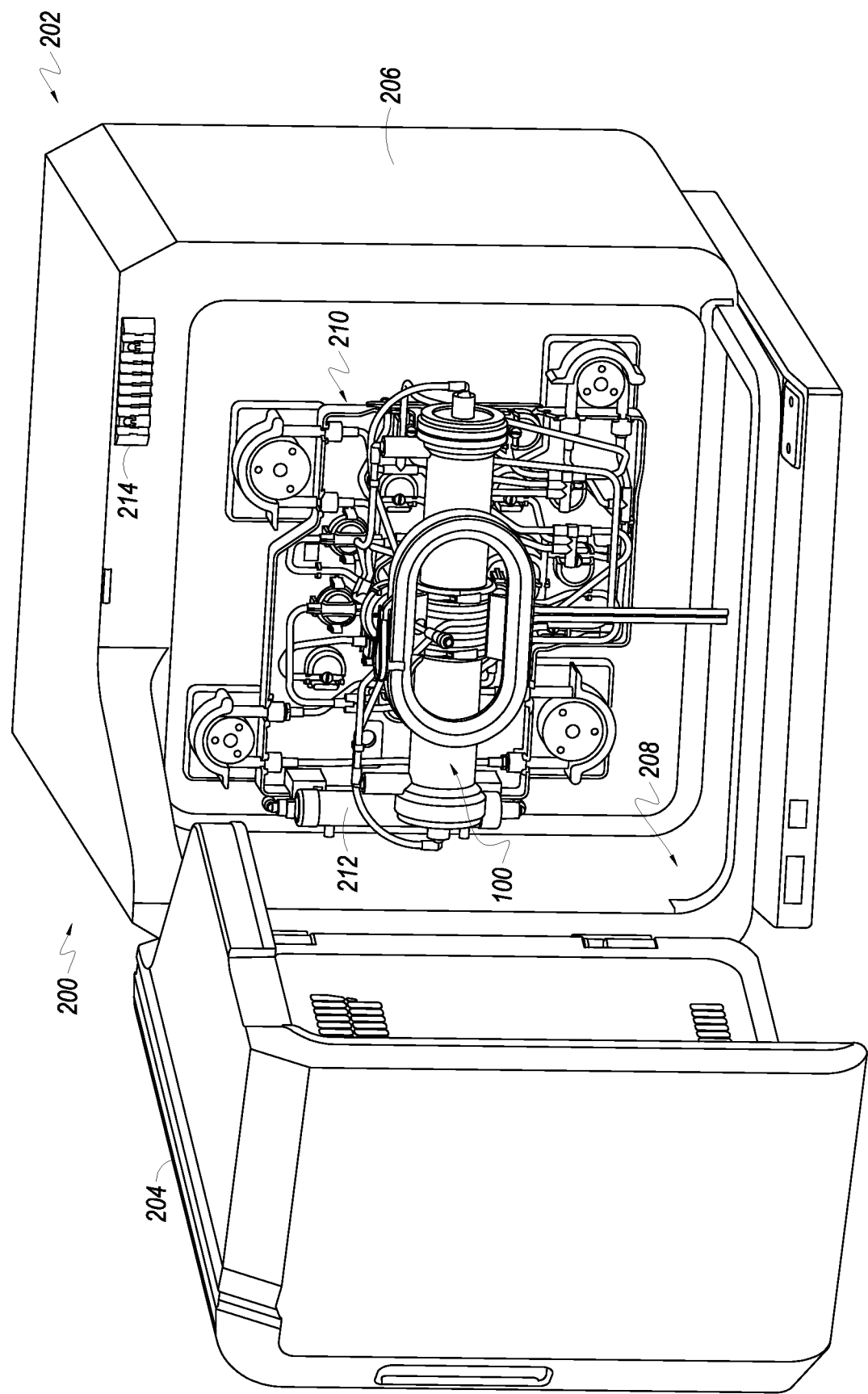
FIG. 2 illustrates a perspective view of a cell expansion system with a premounted fluid conveyance device, in accordance with embodiments.

Turning to FIG. 2, an embodiment of a cell expansion system 200 with a premounted fluid conveyance assembly is shown in accordance with embodiments of the present disclosure. The CES 200 includes a cell expansion machine 202 that comprises a hatch or closable door 204 for engagement with a back portion 206 of the cell expansion machine 202. An interior space 208 within the cell expansion machine 202 includes features adapted for receiving and engaging a premounted fluid conveyance assembly 210 that includes a bioreactor 100. The premounted fluid conveyance assembly 210 may be detachably-attachable to the cell expansion machine 202 to facilitate relatively quick exchange of a new or unused premounted fluid conveyance assembly 210 at a cell expansion machine 202 for a used premounted fluid conveyance assembly 210 at the same cell expansion machine 202. A single cell expansion machine 202 may be operated to grow or expand a first set of cells using a first premounted fluid conveyance assembly 210 and, thereafter, may be used to grow or expand a second set of cells using a second premounted fluid conveyance assembly 210 without needing to be sanitized between interchanging the first premounted fluid conveyance assembly 210 for the second premounted fluid conveyance assembly 210. The premounted fluid conveyance assembly includes a bioreactor 100 and an oxygenator or gas transfer module 212. Tubing guide slots are shown as 214 for receiving various media tubing connected to premounted fluid conveyance assembly 210, according to embodiments.

Figure 3:
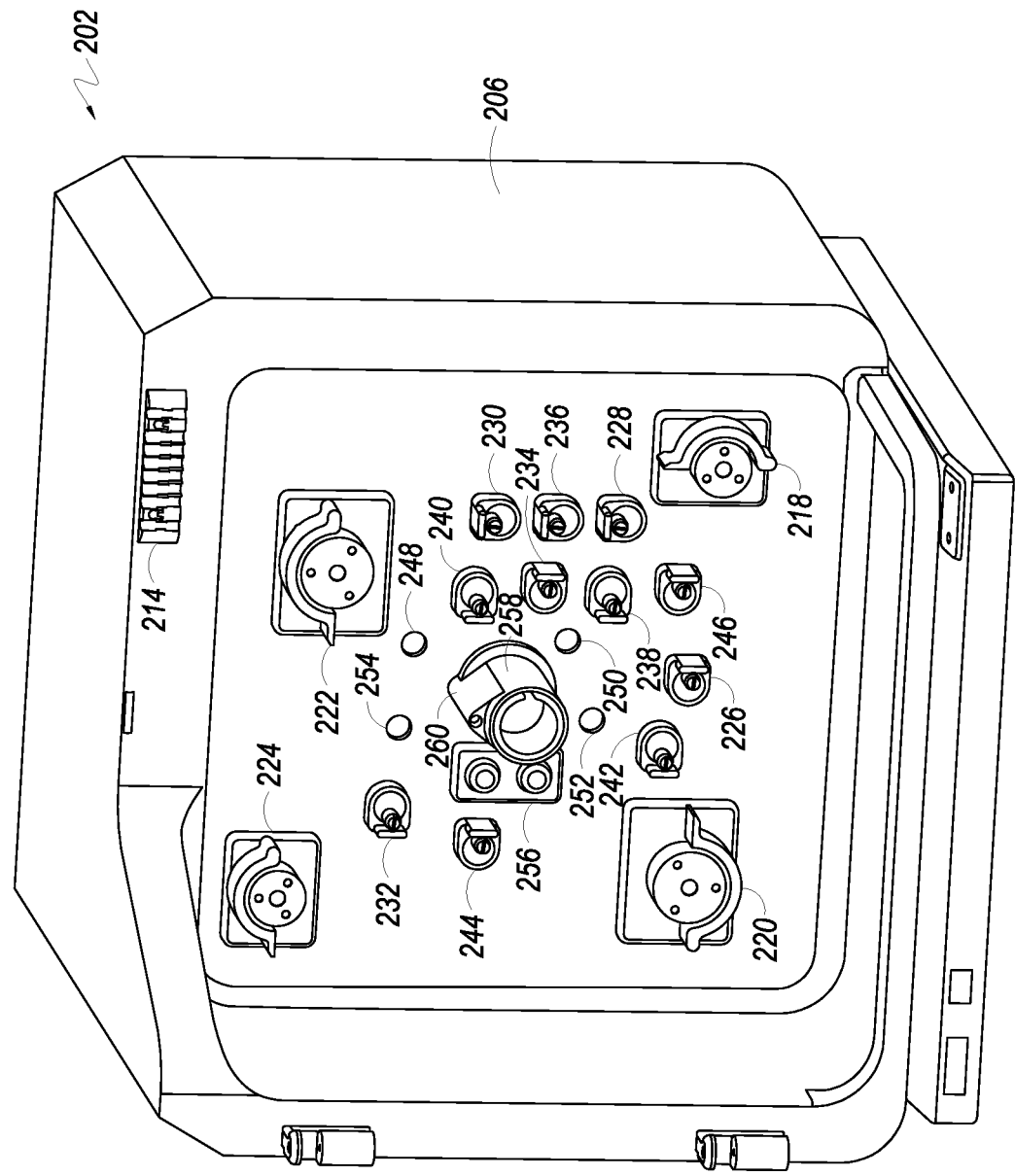
FIG. 3 depicts a perspective view of a housing of a cell expansion system, in accordance with embodiments.

Next, FIG. 3 illustrates the back portion 206 of cell expansion machine 202 prior to detachably-attaching a premounted fluid conveyance assembly 210 (FIG. 2), in accordance with embodiments of the present disclosure. The closable door 204 (shown in FIG. 2) is omitted from FIG. 3. The back portion 206 of the cell expansion machine 202 includes a number of different structures for working in combination with elements of a premounted fluid conveyance assembly 210. More particularly, the back portion 206 of the cell expansion machine 202 includes a plurality of peristaltic pumps for cooperating with pump loops on the premounted fluid conveyance assembly 210, including the IC circulation pump 218, the EC circulation pump 220, the IC inlet pump 222, and the EC inlet pump 224. In addition, the back portion 206 of the cell expansion machine 202 includes a plurality of valves, including the IC circulation valve 226, the reagent valve 228, the IC media valve 230, the air removal valve 232, the cell inlet valve 234, the wash valve 236, the distribution valve 238, the EC media valve 240, the IC waste valve 242, the EC waste valve 244, and the harvest valve 246. Several sensors are also associated with the back portion 206 of the cell expansion machine 202, including the IC outlet pressure sensor 248, the combination IC inlet pressure and temperature sensors 250, the combination EC inlet pressure and temperature sensors 252, and the EC outlet pressure sensor 254. Also shown is an optical sensor 256 for an air removal chamber.

In accordance with embodiments, a shaft or rocker control 258 for rotating the bioreactor 100 is shown in FIG. 3. Shaft fitting 260 associated with the shaft or rocker control 258 allows for proper alignment of a shaft access aperture, see e.g., 424 (FIG. 4) of a tubing-organizer, see e.g., 300 (FIG. 4) of a premounted conveyance assembly 210 or 400 with the back portion 206 of the cell expansion machine 202. Rotation of shaft or rocker control 258 imparts rotational movement to shaft fitting 260 and bioreactor 100. Thus, when an operator or user of the CES 200 attaches a new or unused premounted fluid conveyance assembly 400 (FIG. 4) to the cell expansion machine 202, the alignment is a relatively simple matter of properly orienting the shaft access aperture 424 (FIG. 4) of the premounted fluid conveyance assembly 210 or 400 with the shaft fitting 260.

Figure 4:
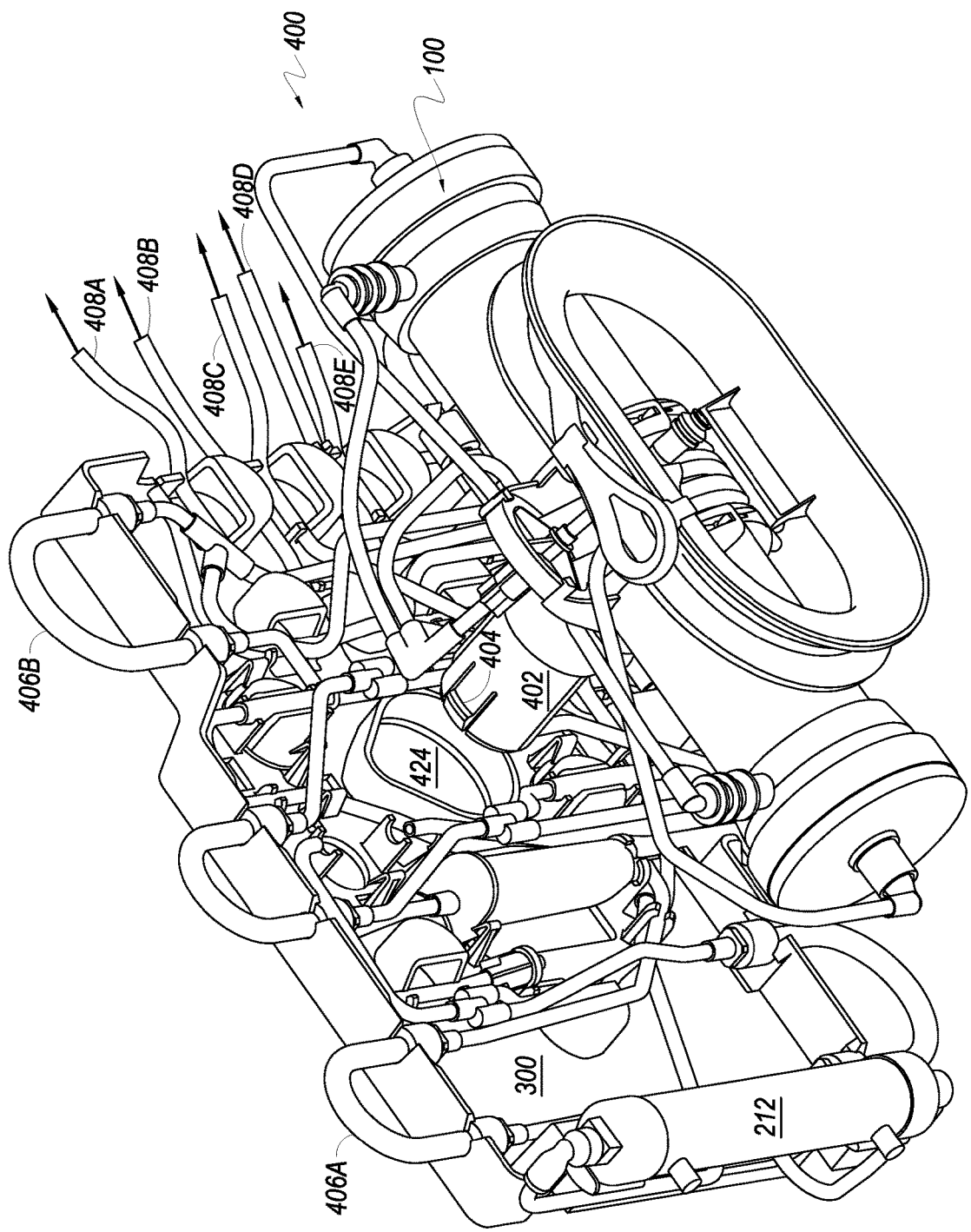
FIG. 4 illustrates a perspective view of a premounted fluid conveyance device, in accordance with embodiments.

Turning to FIG. 4, a perspective view of a detachably-attachable premounted fluid conveyance assembly 400 is shown. The premounted fluid conveyance assembly 400 may be detachably-attachable to the cell expansion machine 202 to facilitate relatively quick exchange of a new or unused premounted fluid conveyance assembly 400 at a cell expansion machine 202 for a used premounted fluid conveyance assembly 400 at the same cell expansion machine 202. As shown in FIG. 4, the bioreactor 100 may be attached to a bioreactor coupling that includes a shaft fitting 402. The shaft fitting 402 includes one or more shaft fastening mechanisms, such as a biased arm or spring member 404 for engaging a shaft, e.g., 258 (shown in FIG. 3), of the cell expansion machine 202.

In embodiments, the shaft fitting 402 and the spring member 404 connect to mechanisms of a cell expansion system that rotate the bioreactor 100. For example, in some embodiments, the cell expansion system may be part of a QUANTUM® Cell Expansion System (CES), manufactured by Terumo BCT, Inc. of Lakewood, Colo., which provides for rotation of a bioreactor. Examples of cell expansion systems that provide for rotation of the bioreactor are described in at least: U.S. Pat. No. 8,399,245, issued Mar. 19, 2013, entitled "ROTATION SYSTEM FOR CELL GROWTH CHAMBER OF A CELL EXPANSION SYSTEM AND METHOD OF USE THEREFOR;" U.S. Pat. No. 8,809,043, issued Feb. 13, 2013, entitled "ROTATION SYSTEM FOR CELL GROWTH CHAMBER OF A CELL EXPANSION SYSTEM AND METHOD OF USE THEREFOR;" and U.S. Pat. No. 9,057,045, issued Jun. 16, 2015, entitled "METHOD OF LOADING AND DISTRIBUTING CELLS IN A BIOREACTOR OF A CELL EXPANSION SYSTEM;" all three of which are hereby incorporated by reference in their entirety as if set forth herein in full.

According to embodiments, the premounted fluid conveyance assembly 400 includes tubing 408A, 408B, 408C, 408D, 408E, etc., and various tubing fittings to provide the fluid paths shown in FIGS. 5-9, as discussed below. Pump loops 406A, 406B, and 406C are also provided for the pump(s). In embodiments, although the various media may be provided at the site where the cell expansion machine 202 is located, the premounted fluid conveyance assembly 400 may include sufficient tubing length to extend to the exterior of the cell expansion machine 202 and to enable welded connections to tubing associated with the media bags, according to embodiments.

Figure 5:
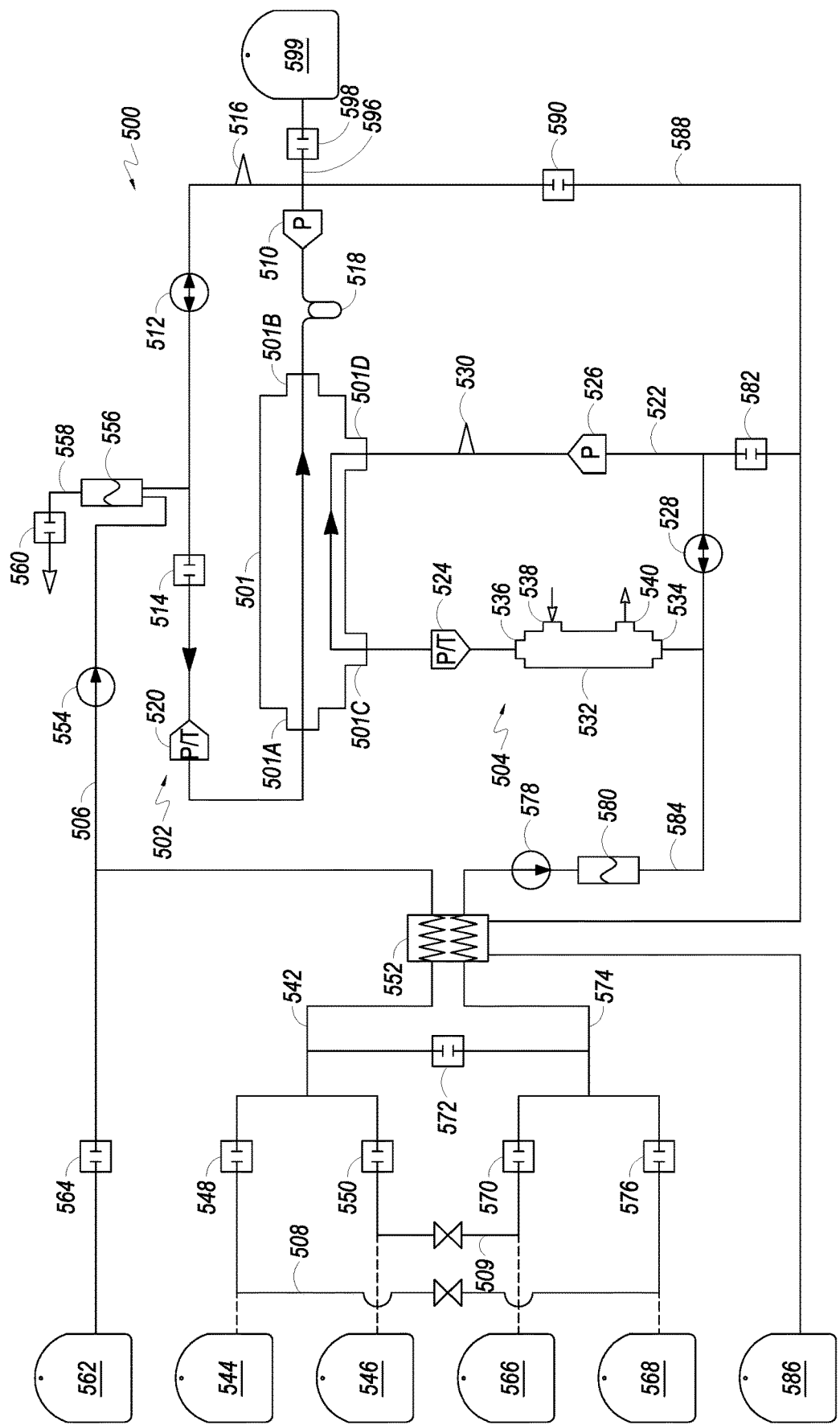
FIG. 5 depicts a schematic of a cell expansion system, in accordance with embodiments.
Figure 6:
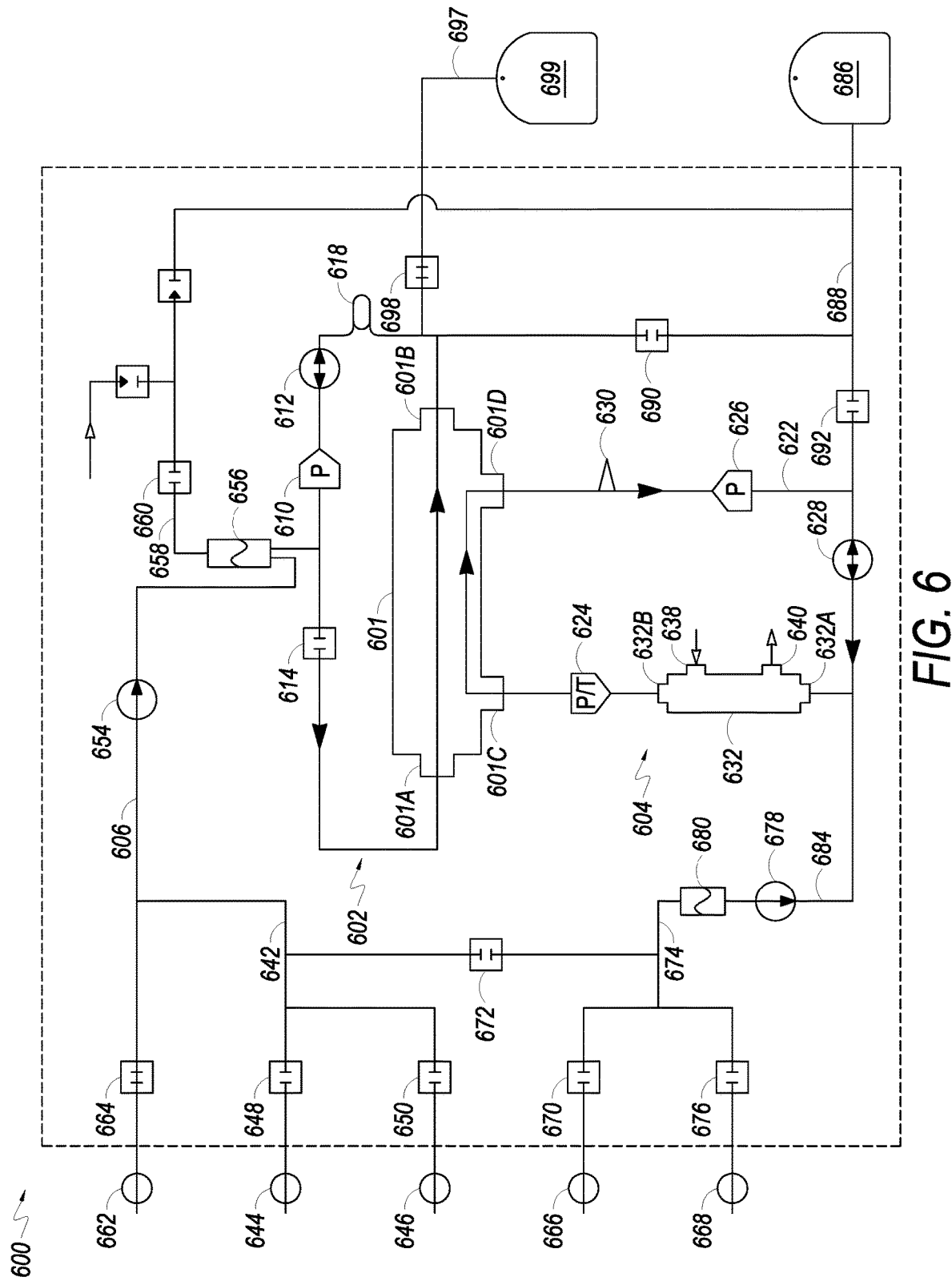
FIG. 6 illustrates a schematic of another embodiment of a cell expansion system.

FIG. 5 illustrates a schematic of an embodiment of a cell expansion system 500, and FIG. 6 illustrates a schematic of another embodiment of a cell expansion system 600. In the embodiments shown in FIGS. 5 and 6, and as described below, the cells are grown in the IC space. However, the disclosure is not limited to such examples and may in other embodiments provide for cells to be grown in the EC space.

FIG. 5 illustrates a CES 500, which includes first fluid circulation path 502 (also referred to as the "intracapillary loop" or "IC loop") and second fluid circulation path 504 (also referred to as the "extracapillary loop" or "EC loop"), according to embodiments. First fluid flow path 506 may be fluidly associated with hollow fiber bioreactor 501 to form, at least in part, first fluid circulation path 502. Fluid flows into hollow fiber bioreactor 501 through IC inlet port 501A, through hollow fibers in hollow fiber bioreactor 501, and exits via IC outlet port 501B. Pressure gauge 510 measures the pressure of media leaving hollow fiber bioreactor 501. Media flows through IC circulation pump 512 which may be used to control the rate of media flow/rate of fluid circulation. IC circulation pump 512 may pump the fluid in a first direction (e.g., clockwise) or second direction opposite the first direction (e.g., counter clockwise). Exit port 501B may be used as an inlet in the reverse direction. Media entering the IC loop 502 may then enter through valve 514. As those skilled in the art will appreciate, additional valves and/or other devices may be placed at various locations to isolate and/or measure characteristics of the media along portions of the fluid paths. Accordingly, it is to be understood that the schematic shown represents one possible configuration for various elements of the CES 500, and modifications to the schematic shown are within the scope of the one or more present embodiments.

With regard to the IC loop 502, samples of media may be obtained from sample port 516 or sample coil 518 during operation. Pressure/temperature gauge 520 disposed in first fluid circulation path 502 allows detection of media pressure and temperature during operation. Media then returns to IC inlet port 501A to complete fluid circulation path 502. Cells grown/expanded in hollow fiber bioreactor 501 may be flushed out of hollow fiber bioreactor 501 into harvest bag 599 through valve 598 or redistributed within the hollow fibers for further growth. This will be described in more detail below.

Fluid in second fluid circulation path 504 enters hollow fiber bioreactor 501 via EC inlet port 501C, and leaves hollow fiber bioreactor 501 via EC outlet port 501D. Media in the EC loop 504 may be in contact with the outside of the hollow fibers in the hollow fiber bioreactor 501, thereby allowing diffusion of small molecules into and out of the hollow fibers.

Pressure/temperature gauge 524 disposed in the second fluid circulation path 504 allows the pressure and temperature of media to be measured before the media enters the EC space of hollow fiber bioreactor 501. Pressure gauge 526 allows the pressure of media in the second fluid circulation path 504 to be measured after it leaves hollow fiber bioreactor 501. With regard to the EC loop, samples of media may be obtained from sample port 530 or a sample coil during operation.

In embodiments, after leaving EC outlet port 501D of hollow fiber bioreactor 501, fluid in second fluid circulation path 504 passes through EC circulation pump 528 to oxygenator or gas transfer module 532. EC circulation pump 528 may also pump the fluid in opposing directions. Second fluid flow path 522 may be fluidly associated with oxygenator or gas transfer module 532 via oxygenator inlet port 534 and oxygenator outlet port 536. In operation, fluid media flows into oxygenator or gas transfer module 532 via oxygenator inlet port 534, and exits oxygenator or gas transfer module 532 via oxygenator outlet port 536. Oxygenator or gas transfer module 532 adds oxygen to and removes bubbles from media in the CES 500. In various embodiments, media in second fluid circulation path 504 may be in equilibrium with gas entering oxygenator or gas transfer module 532. The oxygenator or gas transfer module 532 may be any appropriately sized oxygenator or gas transfer device. Air or gas flows into oxygenator or gas transfer module 532 via filter 538 and out of oxygenator or gas transfer device 532 through filter 540. Filters 538 and 540 reduce or prevent contamination of oxygenator or gas transfer module 532 and associated media. Air or gas purged from the CES 500 during portions of a priming sequence may vent to the atmosphere via the oxygenator or gas transfer module 532.

In the configuration depicted for CES 500, fluid media in first fluid circulation path 502 and second fluid circulation path 504 flows through hollow fiber bioreactor 501 in the same direction (a co-current configuration). The CES 500 may also be configured to flow in a counter-current configuration.

In accordance with at least one embodiment, media, including cells (from bag 562), and fluid media from bag 546 may be introduced to first fluid circulation path 502 via first fluid flow path 506. Fluid container 562 (e.g., Cell Inlet Bag or Saline Priming Fluid for priming air out of the system) may be fluidly associated with the first fluid flow path 506 and the first fluid circulation path 502 via valve 564.

Fluid containers, or media bags, 544 (e.g., Reagent) and 546 (e.g., IC Media) may be fluidly associated with either first fluid inlet path 542 via valves 548 and 550, respectively, or second fluid inlet path 574 via valves 548, 550, and 570. First and second sterile sealable input priming paths 508 and 509 are also provided. An air removal chamber (ARC) 556 may be fluidly associated with first circulation path 502. The air removal chamber 556 may include one or more ultrasonic sensors including an upper sensor and lower sensor to detect air, a lack of fluid, and/or a gas/fluid interface, e.g., an air/fluid interface, at certain measuring positions within the air removal chamber 556. For example, ultrasonic sensors may be used near the bottom and/or near the top of the air removal chamber 556 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 500 during portions of the priming sequence or other protocols may vent to the atmosphere out air valve 560 via line 558 that may be fluidly associated with air removal chamber 556.

EC media (from bag 568) or wash solution (from bag 566) may be added to either the first or second fluid flow paths. Fluid container 566 may be fluidly associated with valve 570 that may be fluidly associated with first fluid circulation path 502 via distribution valve 572 and first fluid inlet path 542. Alternatively, fluid container 566 may be fluidly associated with second fluid circulation path 504 via second fluid inlet path 574 and EC inlet path 584 by opening valve 570 and closing distribution valve 572. Likewise, fluid container 568 may be fluidly associated with valve 576 that may be fluidly associated with first fluid circulation path 502 via first fluid inlet path 542 and distribution valve 572. Alternatively, fluid container 568 may be fluidly associated with second fluid inlet path 574 by opening valve 576 and closing valve distribution 572. An optional heat exchanger 552 may be provided for media reagent or wash solution introduction.

In the IC loop, fluid may be initially advanced by the IC inlet pump 554. In the EC loop, fluid may be initially advanced by the EC inlet pump 578. An air detector 580, such as an ultrasonic sensor, may also be associated with the EC inlet path 584.

In at least one embodiment, first and second fluid circulation paths 502 and 504 are connected to waste line 588. When valve 590 is opened, IC media may flow through waste line 588 and to waste or outlet bag 586. Likewise, when valve 582 is opened, EC media may flow through waste line 588 to waste or outlet bag 586.

In embodiments, cells may be harvested via cell harvest path 596. Here, cells from hollow fiber bioreactor 501 may be harvested by pumping the IC media containing the cells through cell harvest path 596 and valve 598 to cell harvest bag 599.

Various components of the CES 500 may be contained or housed within a machine or housing, such as cell expansion machine 202 (FIGS. 2 and 3), wherein the machine maintains cells and media at a predetermined temperature.

Turning to FIG. 6, a schematic of another embodiment of a cell expansion system 600 is shown. CES 600 includes a first fluid circulation path 602 (also referred to as the "intracapillary loop" or "IC loop") and second fluid circulation path 604 (also referred to as the "extracapillary loop" or "EC loop"). First fluid flow path 606 may be fluidly associated with hollow fiber bioreactor 601 to form first fluid circulation path 602. Fluid flows into hollow fiber bioreactor 601 through IC inlet port 601A, through hollow fibers in hollow fiber bioreactor 601, and exits via IC outlet port 601B. Pressure sensor 610 measures the pressure of media leaving hollow fiber bioreactor 601. In addition to pressure, sensor 610 may, in embodiments, also be a temperature sensor that detects the media pressure and temperature during operation.

Media flows through IC circulation pump 612 which may be used to control the rate of media flow or rate of circulation. IC circulation pump 612 may pump the fluid in a first direction (e.g. counter clockwise) or second direction opposite the first direction (e.g., clockwise). Exit port 601B may be used as an inlet in the reverse direction. Media entering the IC loop may flow through valve 614. As those skilled in the art will appreciate, additional valves and/or other devices may be placed at various locations to isolate and/or measure characteristics of the media along portions of the fluid paths. Samples of media may be obtained from sample coil 618 during operation. Media then returns to IC inlet port 601A to complete fluid circulation path 602.

Cells grown/expanded in hollow fiber bioreactor 601 may be flushed out of hollow fiber bioreactor 601 into harvest bag 699 through valve 698 and line 697. Alternatively, when valve 698 is closed, the cells may be redistributed within hollow fiber bioreactor 601 for further growth. It is to be understood that the schematic shown represents one possible configuration for various elements of the CES 600, and modifications to the schematic shown are within the scope of the one or more present embodiments.

Fluid in second fluid circulation path 604 enters hollow fiber bioreactor 601 via EC inlet port 601C and leaves hollow fiber bioreactor 601 via EC outlet port 601D. Media in the EC loop may be in contact with the outside of the hollow fibers in the hollow fiber bioreactor 601, thereby allowing diffusion of small molecules into and out of the hollow fibers that may be within chamber 601, according to an embodiment.

Pressure/temperature sensor 624 disposed in the second fluid circulation path 604 allows the pressure and temperature of media to be measured before the media enters the EC space of the hollow fiber bioreactor 601. Sensor 626 allows the pressure and/or temperature of media in the second fluid circulation path 604 to be measured after it leaves the hollow fiber bioreactor 601. With regard to the EC loop, samples of media may be obtained from sample port 630 or a sample coil during operation.

After leaving EC outlet port 601D of hollow fiber bioreactor 601, fluid in second fluid circulation path 604 passes through EC circulation pump 628 to oxygenator or gas transfer module 632. EC circulation pump 628 may also pump the fluid in opposing directions, according to embodiments. Second fluid flow path 622 may be fluidly associated with oxygenator or gas transfer module 632 via an inlet port 632A and an outlet port 632B of oxygenator or gas transfer module 632. In operation, fluid media flows into oxygenator or gas transfer module 632 via inlet port 632A, and exits oxygenator or gas transfer module 632 via outlet port 632B. Oxygenator or gas transfer module 632 adds oxygen to and removes bubbles from media in the CES 600.

In various embodiments, media in second fluid circulation path 604 may be in equilibrium with gas entering oxygenator or gas transfer module 632. The oxygenator or gas transfer module 632 may be any appropriately sized device useful for oxygenation or gas transfer. Air or gas flows into oxygenator or gas transfer module 632 via filter 638 and out of oxygenator or gas transfer device 632 through filter 640. Filters 638 and 640 reduce or prevent contamination of oxygenator or gas transfer module 632 and associated media. Air or gas purged from the CES 600 during portions of a priming sequence may vent to the atmosphere via the oxygenator or gas transfer module 632.

In the configuration depicted for CES 600, fluid media in first fluid circulation path 602 and second fluid circulation path 604 flows through hollow fiber bioreactor 601 in the same direction (a co-current configuration). The CES 600 may also be configured to flow in a counter-current configuration.

In accordance with at least one embodiment, media, including cells (from a source such as a cell container, e.g. a bag) may be attached at attachment point 662, and fluid media from a media source may be attached at attachment point 646. The cells and media may be introduced into first fluid circulation path 602 via first fluid flow path 606. Attachment point 662 may be fluidly associated with the first fluid flow path 606 via valve 664, and attachment point 646 may be fluidly associated with the first fluid flow path 606 via valve 650. A reagent source may be fluidly connected to point 644 and be associated with fluid inlet path 642 via valve 648, or second fluid inlet path 674 via valves 648 and 672.

Air removal chamber (ARC) 656 may be fluidly associated with first circulation path 602. The air removal chamber 656 may include one or more sensors including an upper sensor and lower sensor to detect air, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 600 during portions of a priming sequence or other protocol(s) may vent to the atmosphere out air valve 660 via line 658 that may be fluidly associated with air removal chamber 656.

An EC media source may be attached to EC media attachment point 668 and a wash solution source may be attached to wash solution attachment point 666, to add EC media and/or wash solution to either the first or second fluid flow path. Attachment point 666 may be fluidly associated with valve 670 that may be fluidly associated with first fluid circulation path 602 via valve 672 and first fluid inlet path 642. Alternatively, attachment point 666 may be fluidly associated with second fluid circulation path 604 via second fluid inlet path 674 and second fluid flow path 684 by opening valve 670 and closing valve 672. Likewise, attachment point 668 may be fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing valve distribution 672.

In the IC loop, fluid may be initially advanced by the IC inlet pump 654. In the EC loop, fluid may be initially advanced by the EC inlet pump 678. An air detector 680, such as an ultrasonic sensor, may also be associated with the EC inlet path 684.

In at least one embodiment, first and second fluid circulation paths 602 and 604 are connected to waste line 688. When valve 690 is opened, IC media may flow through waste line 688 and to waste or outlet bag 686. Likewise, when valve 692 is opened, EC media may flow to waste or outlet bag 686.

After cells have been grown in hollow fiber bioreactor 601, they may be harvested via cell harvest path 697. Here, cells from hollow fiber bioreactor 601 may be harvested by pumping the IC media containing the cells through cell harvest path 697, with valve 698 open, into cell harvest bag 699.

Various components of the CES 600 may be contained or housed within a machine or housing, such as cell expansion machine 202 (FIGS. 2 and 3), wherein the machine maintains cells and media at a predetermined temperature. It is further noted that, in embodiments, components of CES 600 and CES 500 (FIG. 5) may be combined. In other embodiments, a CES may include fewer or additional components than those shown in FIGS. 5 and 6 and still be within the scope of the present disclosure. In embodiments, portions of CES 500 and 600 may be implemented by one or more features of the QUANTUM® Cell Expansion System (CES), manufactured by Terumo BCT, Inc. of Lakewood, Colo.

Examples and further description of cell expansion systems are provided in U.S. patent application Ser. No. 12/042, 798 (U.S. Pat. No. 8,309,347), entitled, "Cell Expansion System and Methods of Use," issued on Nov. 13, 2012, which is hereby incorporated by reference herein in its entirety as if set forth herein in full.

In one specific embodiment of using CES 600, a process for coating bioreactor 601 may be performed prior to growing of cells in the bioreactor. As described above, various cell types may be grown in CES 600. For example, adherent cells such as human mensenchymal stem cells (hMSC's) may be expanded. As part of expanding hMSC's, a process for preparing surfaces of the bioreactor to allow adherent cells to attach may be performed. In these embodiments, one or more reagents may be circulated through bioreactor 601 to coat portions of the bioreactor 601 with the reagent, which may enhance the surface to allow adherent cells to attach to the surface and grow.

In some embodiments, the reagent may include one or more glycoproteins, e.g., fibronectin. In embodiments, the reagent may be isolated and added to the CES 600 as an isolated reagent. In other embodiments, a combination of materials, such as may be found in cryoprecipitate, platelet lysate, collagen, etc. may be introduced into the CES 600. These are merely some examples, and embodiments of the present invention are not limited thereto.

In embodiments, the reagent may be added to the CES 600 using a fluid that includes the reagent. In addition, several steps may be performed to promote coating of the bioreactor with the reagent. For example, the fluid with the reagent may be circulated through the bioreactor at different flow rates and in different directions (e.g., clockwise and/or counterclockwise). In addition, the bioreactor may be rotated before, during, or after circulation of the fluid.

It is noted that in some embodiments, the reagent may be added to bioreactor 601, after a priming step. As may be appreciated, the priming step may be used to push air and/or other gasses out of the CES 600 and bioreactor 601 before fluid with the reagent is circulated.

Once in the bioreactor 601, the fluid with the reagent may be circulated through the bioreactor. In one embodiment, the circulation of the fluid/reagent may be designed to promote the coating of as much surface area as possible in the bioreactor. Accordingly, the fluid/reagent may be circulated at different flow rates After the bioreactor 601 has been coated with the reagent, cells may be introduced into the bioreactor with some nutrients and/or other material for expanding the cells. During the expansion, there may be a number of materials that may be added or removed from bioreactor 601. As one example, additional proteins, nutrients, gasses (e.g., cytokines) may be may be added to bioreactor 601. The additional material may be added individually, at the same time, at different times, or may be combined and added in combination. After the cells have been expanded, the cells may be removed from the bioreactor 601 and may be collected in container 699.

In some embodiments, use of CES 600 may provide advantages (in growing cells) over conventional processes. For example, the use of hollow fibers allows close cell to cell communication, which may enhance the growth of the cells to start and continue to proliferate. Also, the use of a hollow fiber bioreactor, such as bioreactor 601, may provide a large surface area for cell growth, which may yield a higher concentration or higher volume of cells.

Further, the conditions in bioreactor 601 may be controlled using a number of different components of the CES 600, including IC flow rates and EC flow rates. Also, CES 600 provides various locations for the addition of materials, which allows more direct, or indirect (e.g., perfusion) of proteins, nutrients, supplements, etc. into bioreactor 601.

Additionally, CES 600 provides a closed system. That is, the steps for growing the cells may be performed without direct exposure to the ambient environment, which may contaminate the cells, or be contaminated by the cells or materials used in growing the cells.

Figure 7:
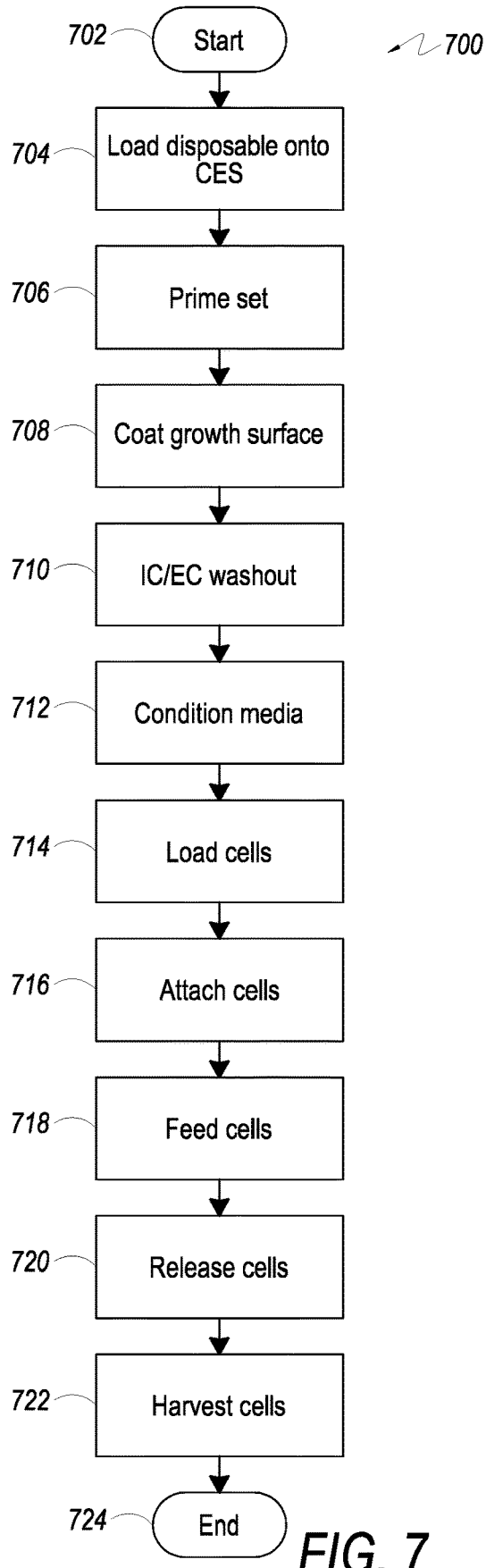
FIG. 7 illustrates a flow of a process for growing cells in a bioreactor according to embodiments.

FIG. 7 illustrates flow 700 that may be performed in embodiments to expand cells in a CES that includes a bioreactor. Although specific devices may be described below for performing steps in flow 700, embodiments are not limited thereto. For example, some steps may be described as performed by parts of a cell expansion system (e.g., CES 10, CES 500, CES 600) or a computer system (1500 (FIG. 15)) or parts of a computer system (e.g., processor 1512 (FIG. 15)), which may execute steps based on software provided as processor executable instructions. This is done merely for illustrative purposes, and flow 700 is not limited to being performed by any specific device.

FIG. 7 illustrates example flow 700 with operational steps of a process for growing and harvesting cells in a cell expansion system, such as CES 500 (FIG. 5) or CES 600 (FIG. 6), in accordance with embodiments of the present disclosure. Flow 700 starts at 702, and flow 700 proceeds to load the disposable tubing set 704 onto the cell expansion system. In embodiments, this may be performed by a user or an operator of a CES (e.g., CES 500 or CES 600).

Next, the system may be primed 706. In an embodiment, a user or an operator, for example, may provide an instruction to the system to prime by selecting a task for priming, for example. In an embodiment, such task for priming may be a pre-programmed task. The system 500 (FIG. 5) or 600 (FIG. 6) may be primed, for example, with Phosphate-buffered saline (PBS). To prime the bioreactor 501, 601, a bag (546) may be attached (for example, to connection point 646) to the system 500, 600. When referring to numerals in the figures, for example, such as "Numeral, Numeral" (e.g., 500, 600), such nomenclature is intended to mean "Numeral and/or Numeral" (e.g., 500 and/or 600). Valve 550, 650 may be opened. The PBS can then be directed into the first fluid circulation path 502, 602 by the IC inlet pump 554, 654 set to pump the PBS into the first fluid circulation path 502, 602. Valve 514, 614 may be opened while the PBS enters the bioreactor 501, 601 through the inlet 501A, 601A and out of the outlet 501B, 601B. Once the bioreactor 501, 601 and/or the first fluid circulation path 502, 602 have media therein with air removed by the air removal chamber 556, 656, the bioreactor 501, 601 is primed, according to an embodiment.

To further prime the bioreactor 501, 601, a bag 568 may be attached (for example, to connection point 668) to the system 500, 600. Valve 576, 676 may be opened. A media, e.g., PBS, can then be directed into the second fluid circulation path 504, 604 by the EC inlet pump 578, 678 set to pump the media into the second fluid circulation path 504, 604. Valve 582, 692 may be closed while the media enters the bioreactor 601 through the inlet 501C, 601C and out of the outlet 501D, 601D of the EC loop. Once the bioreactor 501, 601 and/or the second fluid circulation path 504, 604 have media with air removed, e.g., by an air removal chamber, the bioreactor 501, 601 is primed, according to an embodiment.

Flow 700 then proceeds to coat the cell growth surface, e.g., bioreactor 501, 601, in step 708, in which the cell growth surface may be coated with a coating agent or reagent. Any coating agent or reagent understood by those of skill in the art may be used, such as a glycoprotein, (e.g., fibronectin, cryoprecipitate, and/or collagen) for example. In an embodiment, an outlet or waste valve 590, 690 to one of the circulation loops, e.g., IC loop 502, 602, may be closed, while the outlet or waste valve 582, 692 to the other circulation loop, e.g., EC loop 504, 604, remains open. For example, the IC waste or outlet valve 590, 690 may be closed while the EC waste or outlet valve 582, 692 is open. In embodiments, a coating agent or reagent may be loaded into a circulation loop, e.g., IC loop 502, 602, of the cell expansion system 500, 600 until the reagent bag 568 or container is empty. Next, the reagent may be chased from an air removal chamber 556, 656 into the circulation loop, e.g., IC loop 502, 602. The bioreactor 501, 601, e.g., cell growth surface of hollow fibers where a hollow fiber bioreactor is used, may then be coated by controlling the fluid movement in the bioreactor 501, 601.

In embodiments, as described in greater detail below, the fluid movement may be controlled by changing flow rates, direction of fluid flow, and/or rotation of the bioreactors 501, 601. In some embodiments, the coating procedure may be referred to as a bulls-eye coat procedure. Embodiments/examples of bulls-eye coat procedures are described in greater detail below with respect to FIGS. 8, 10, and 11.

In other embodiments, fluid movement may use ultrafiltration, such as positive ultrafiltration, to move fluid from one side (e.g., the IC side 502, 602) of the bioreactor 501, 601 to the other side (e.g., the EC side 504, 604). For example, where the IC outlet or waste valve 590, 690 may be closed, with the EC outlet or waste valve open 582, 692, a fluid in the bioreactor 501, 601 may have no pathway but through the pores of the fibers (IC outlet valve 590, 690 closed). In an embodiment, the IC inlet rate may be set to wash the IC side 502, 602 with media or a fluid, such as phosphate buffered saline (PBS), for example. Accordingly, the solution may then flow through the pores of the fibers from the IC side 502, 602 to the EC side 504, 604. The coating agent solution, e.g., CPPT solution, may be hydrostatically deposited onto the inner wall(s) of the bioreactor fiber for a defined time period. For example, such time period may be about ten (10) minutes, according to an embodiment. Other time periods may apply according to other embodiments. Such membrane ultrafiltration method allows adherence promoting proteins to be physisorbed on the bioreactor fibers as the solution flows through the pores of the fiber from the IC side 502, 602 to the EC side 504, 604.

Once the bioreactor is coated, the IC/EC Washout task may be performed in step 710, in which fluid on the IC circulation loop 502, 602 and on the EC circulation loop 504, 604 may be replaced. The replacement volume may be determined by the number of IC Volumes and EC Volumes exchanged.

Next, to maintain a desired gas concentration across the fibers in the bioreactor membrane, the condition media task 712 may be executed to allow the media to reach equilibrium with the provided gas supply before cells are loaded into the bioreactor. For example, rapid contact between the media and the gas supply provided by the gas transfer module or oxygenator 532, 632 is provided by using a high EC circulation rate. The system 500, 600 may then be maintained in a proper or desired state until a user or operator, for example, is ready to load cells into the bioreactor 501, 601. In an embodiment, the system 500, 600 may be conditioned with complete media, for example. Complete media may be any media source used for cell growth. In an embodiment, complete media may comprise alpha-MEM (α-MEM) and fetal bovine serum (FBS), for example. Any type of media known to those of skill in the art may be used.

In embodiments, the condition media task 712 may be a two-step process where, in the first step, the system 500, 600 provides rapid contact between the media and the gas supply by using a high EC circulation rate. In the second step, the system 500, 600 may maintain the bioreactor 501, 601 in a state until the operator is ready to load the cells.

Flow 700 next proceeds to loading cells 714 into the bioreactor 501, 601 from a cell inlet bag 562 (at connection point 662), for example. In an embodiment, the cells are loaded with a uniform suspension 714. In an embodiment, the cells may be loaded into the bioreactor 501, 601 from the cell inlet bag cell inlet bag 562 (at connection point 662) until the bag 562 is empty. Cells may then be chased from the air removal chamber 556, 656 to the bioreactor 501, 601, according to an embodiment. In embodiments that utilize larger chase volumes, cells may be spread and move toward the outlet port 501B, 601B. The distribution of cells may be promoted across the membrane via IC circulation, such as through an IC circulation pump 512, 612, with no IC inlet, for example. Examples and further description of loading and distributing cells are provided in U.S. patent application Ser. No. 13/971,500 (U.S. Pat. No. 9,175,259), entitled, "Method of Loading and Distributing Cells in a Bioreactor of a Cell Expansion System," issued Nov. 3, 2015, which is hereby incorporated by reference herein in its entirety for all that it teaches and for all purposes.

In another embodiment, the cells may be loaded 714 using another type of cell loading, such as a high flux cell load. In yet another embodiment, the cells may be loaded 714 using another type of loading, such as a bulls-eye cell loading technique. Examples and further description of bulls-eye cell loading procedure(s) are provided in U.S. patent application Ser. No. 14/542,276 (U.S. Pat. No. 9,175,259), entitled, "Expanding Cells in a Bioreactor," issued on Apr. 11, 2017, which is hereby incorporated by reference herein in its entirety for all that it teaches and for all purposes.

Further, the cells, e.g., adherent cells, may be allowed to attach 716 to the hollow fibers. In an embodiment, in allowing the cells to attach 716, adherent cells are enabled to attach to the bioreactor membrane while allowing flow on the EC circulation loop 504, 604, with the pump 554, 654 flow rate to the IC loop 502, 602 set to zero. In some embodiments, step 716 and step 714 may be combined in various combinations. For example, in a bulls-eye load process, the loading of the cells 714 may include periods of time where the pump 512, 612 is deactivated and cells are allowed to attach. This may be followed by activation of pump 512, 612 to circulate fluid in the IC loop.

Next, the cells may be fed in step 718, in which a flow rate, e.g., low flow rate in an embodiment, is continuously added to the IC circulation loop 502, 602 and/or the EC circulation loop 504, 604. In an embodiment, the cells may be fed with media, such as media with protein, for example. Outlet settings allow for the removal of fluid added to the system, in accordance with embodiments.

When it is determined to harvest the expanded cells, such as after the cells have reached confluence, after a defined period of time, according to user preference, etc., flow 700 proceeds to release cells 720, in which the cells may be released from the membrane of the bioreactor 501, 601 and may be suspended in the IC loop 502, 602. Following the release of any adherent cells, harvest operation 722 transfers the cells in suspension from the IC circulation loop 502, 602, including any cells remaining in the bioreactor 501, 601, to a harvest bag 599, 699 or other container. Flow 700 then ends at 724.

The releasing of cells 720 and harvesting of those cells 722 may be a five-step process, according to embodiments. A first step in the releasing of cells 720 may perform an IC/EC Washout task in preparation for adding a reagent. For example, IC/EC media may be replaced with a phosphate buffered saline (PBS) to remove protein, calcium (Ca2+), and magnesium (Mg2+) in preparation for adding trypsin, or another chemical-releasing agent, to release any adherent cells. A second step of the releasing cell process 720 includes loading a reagent into the system 500, 600 until the reagent bag 544 is empty. A third step in the releasing cell process can chase the reagent into the IC loop 502, 602. A fourth step in the releasing cell process 720 can mix the reagent within the IC loop 502, 602. A fifth step may generally be a harvest step 722. As described above, following release step 720 and harvest step 722, flow 700 terminates at 724.

Figure 8:
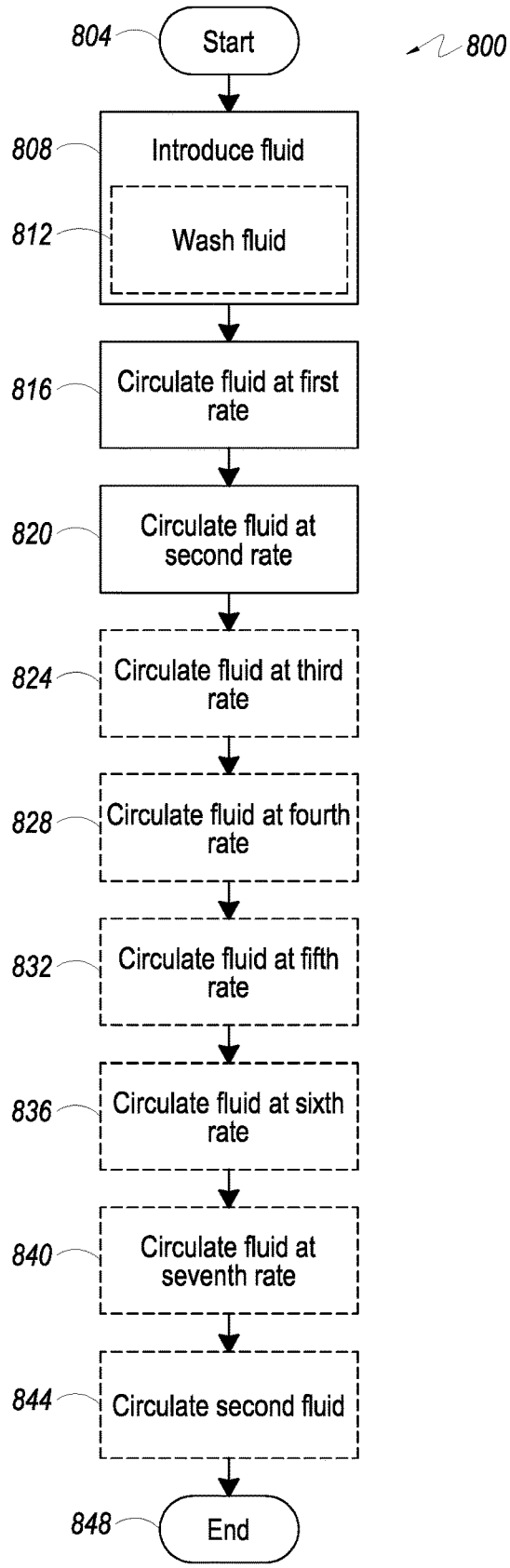
FIG. 8 illustrates a flow for a process of coating a bioreactor according to an embodiment.
Figure 10:
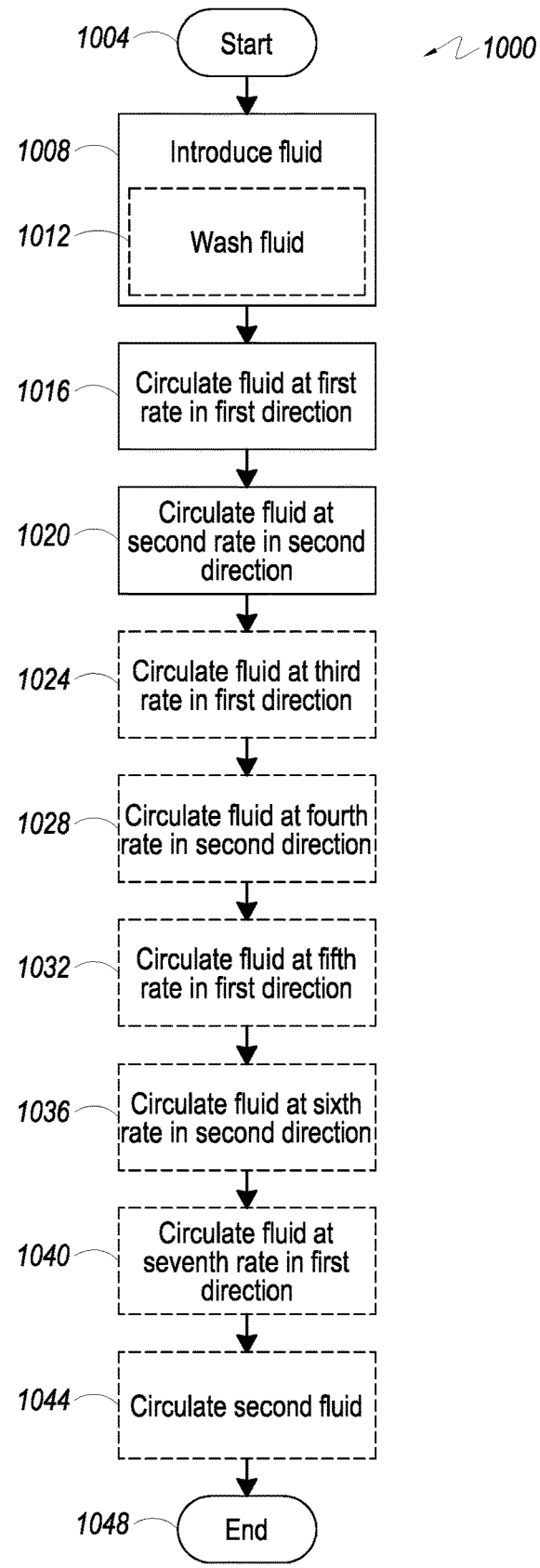
FIG. 10 illustrates a flow for a process of coating a bioreactor according to another embodiment.
Figure 11:
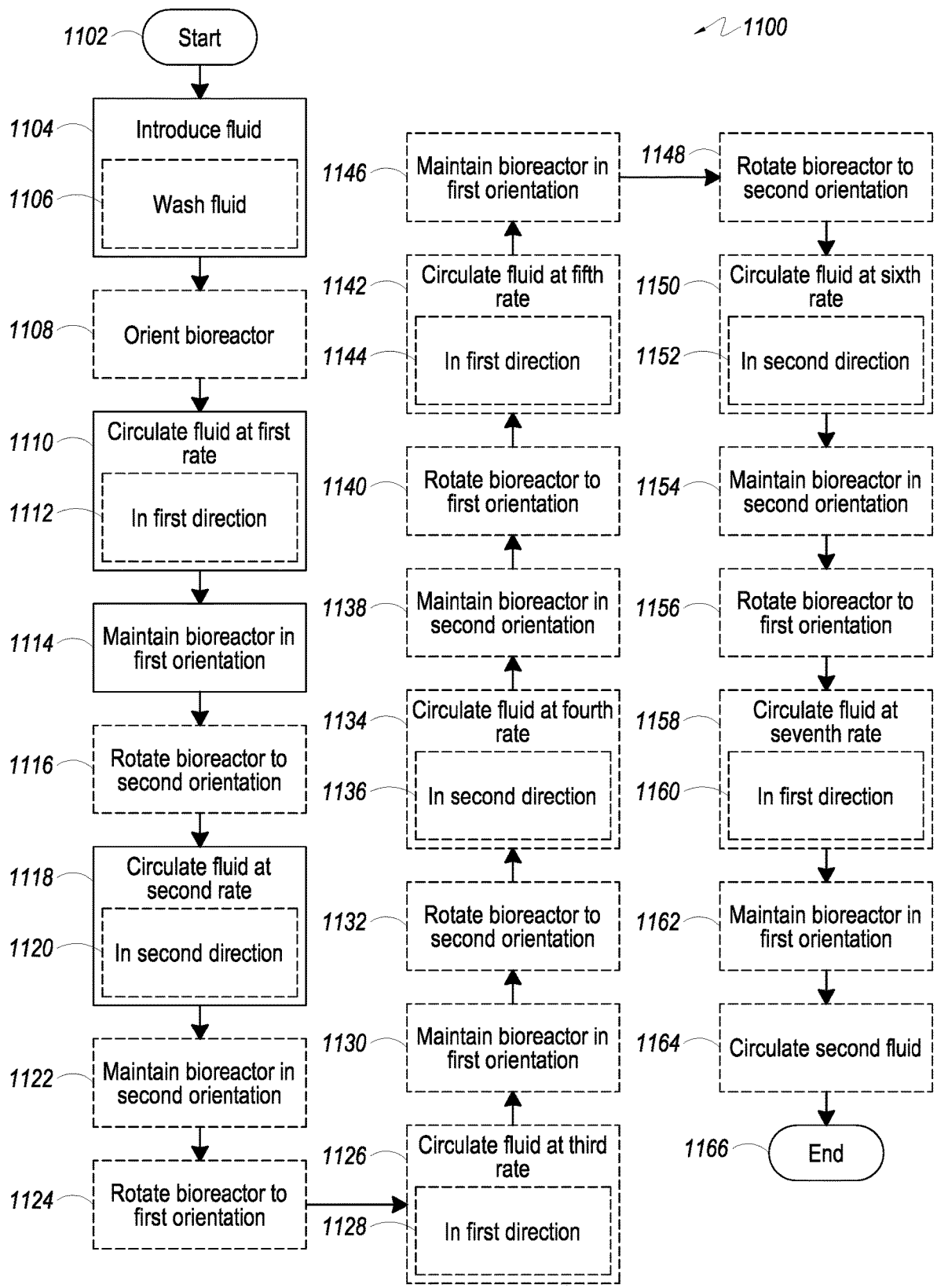
FIG. 11 illustrates a flow for a process of coating a bioreactor according to yet another embodiment.

FIGS. 8, 10, and 11, illustrate flows 800, 1000, and 1100 that may be performed in embodiments to coat a growth surface in a bioreactor. In embodiments, flows 800, 1000, and 1100 may be performed as part of a larger process of expanding cells, such as flow 700 (FIG. 7). In one embodiment, one or more steps of flows 800, 1000, and 1100 may be performed in performing steps 708 and/or 710 of flow 700. Although specific devices may be described below for performing steps in flows 800, 1000, and 1100, embodiments are not limited thereto. For example, some steps may be described as performed by parts of a cell expansion system (e.g., CES 10, CES 500, CES 600) or a computer system (1500 (FIG. 15)) or parts of a computer system (e.g., processor 1512 (FIG. 15)), which may execute steps based on software provided as processor executable instructions.

Referring now to flow 800, it starts at step 804 and proceeds to step 808 where fluid that includes a reagent may be introduced into a cell expansion system and a bioreactor such as bioreactors 100, 501, and/or 601. In embodiments, step 808 may involve activating one or more pumps (554, 654) to introduce fluid with the reagent from a bag (546) or connection point (646) into a fluid flow path.

As part of introducing the fluid with the reagent into the cell expansion system, step 808 may involve optional step 812, where a wash fluid (e.g., PBS) may be used to chase reagent from parts of the CES into bioreactor 501, 601. For example, the wash fluid may flow through path 506, 606 to move any reagent left behind in an ARC, such as ARC 556/656. The wash fluid may chase any lingering reagent into the bioreactor and/or the IC loop associated with the bioreactor, e.g., 502/602.

Flow 800 then passes to step 816 where fluid that includes a reagent may be circulated through a bioreactor such as bioreactors 100, 501, and/or 601. In embodiments, step 816 may involve activating one or more pumps to circulate fluid with the reagent through the bioreactor. For example, an IC circulation pump (e.g., 512 or 612) may be activated to circulate fluid through the IC side of a bioreactor at a first circulation flow rate. In at least one embodiment, fluid may pass through hollow fibers (e.g., the lumen of the hollow fibers).

In embodiments, the first rate may be a relatively high flow rate. In embodiments, the first circulation flow rate may be less than about 500 ml/min, less than about 400 ml/min, or even less than about 300 ml/min. In other embodiments, the first circulation rate may be greater than about 50 ml/min, greater than about 100 ml/min, or even greater than about 150 ml/min. In one embodiment, the first circulation flow rate is between about 100 ml/min and about 500 ml/min, such as about 300 ml/min.

Step 816 may be performed for a first predetermined period of time. In one specific example, the first period of time may be about 4 minutes, about 8 minutes, about 12 minutes, or even about 16 minutes. In other embodiments, the first predetermined period of time may be less than about 20 minutes, less than about 15 minutes, less than about 10 minutes, or even less than about 5 minutes. In some embodiments, the first predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 816 may be performed in embodiments to provide time to allow the reagent to coat portions of the bioreactor. For example, when the bioreactor comprises hollow fibers, step 816 may be performed to allow the reagent time to coat interior surfaces of the hollow fibers.

Flow 800 passes to step 820, wherein fluid with the reagent is circulated at a second flow rate, which may be less than the first flow rate. In embodiments, the second flow rate may be less than about 400 ml/min, less than about 300 ml/min, or even less than about 200 ml/min. In other embodiments, the second circulation rate may be greater than about 25 ml/min, greater than about 50 ml/min, or even greater than about 75 ml/min. In one embodiment, the second circulation flow rate is between about 100 ml/min and about 300 ml/min, such as about 250 ml/min.

Step 820 may be performed for a second predetermined period of time. In one specific example, the second period of time may be about 4 minutes, about 8 minutes, about 12 minutes, or even about 16 minutes. In other embodiments, the second predetermined period of time may be less than about 20 minutes, less than about 15 minutes, less than about 10 minutes, or even less than about 5 minutes. In some embodiments, the second predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 820 may be performed in embodiments to provide time to allow the reagent to coat portions of the bioreactor. For example, when the bioreactor comprises hollow fibers, step 820 may be performed to allow the reagent time to coat interior surfaces of the hollow fibers.

Flow 800 passes to optional step 824, wherein fluid with the reagent is circulated at a third flow rate, which may be less than the first flow rate. In embodiments, the third flow rate may be less than the second flow rate. In embodiments, the third flow rate may be less than about 350 ml/min, less than about 300 ml/min, or even less than about 250 ml/min. In other embodiments, the second circulation rate may be greater than about 25 ml/min, greater than about 50 ml/min, or even greater than about 75 ml/min. In one embodiment, the third circulation flow rate is between about 50 ml/min and about 250 ml/min, such as about 200 ml/min.

Optional step 824 may be performed for a third predetermined period of time. In one specific example, the second period of time may be about 4 minutes, about 8 minutes, about 12 minutes, or even about 16 minutes. In other embodiments, the third predetermined period of time may be less than about 20 minutes, less than about 15 minutes, less than about 10 minutes, or even less than about 5 minutes. In some embodiments, the third predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 824 may be performed in embodiments to provide time to allow the reagent to coat portions of the bioreactor. For example, when the bioreactor comprises hollow fibers, step 824 may be performed to allow the reagent time to coat interior surfaces of the hollow fibers.

Flow 800 then passes to optional step 828, where fluid with the reagent is circulated at a fourth flow rate, which may be less than the third flow rate. In embodiments, the fourth flow rate may be less than about 250 ml/min, less than about 200 ml/min, or even less than about 150 ml/min. In other embodiments, the second circulation rate may be greater than about 25 ml/min, greater than about 50 ml/min, or even greater than about 75 ml/min. In one embodiment, the fourth circulation flow rate is between about 25 ml/min and about 200 ml/min, such as about 150 ml/min.

Optional step 828 may be performed for a fourth predetermined period of time. In one specific example, the second period of time may be about 4 minutes, about 8 minutes, about 12 minutes, or even about 16 minutes. In other embodiments, the fourth predetermined period of time may be less than about 20 minutes, less than about 15 minutes, less than about 10 minutes, or even less than about 5 minutes. In some embodiments, the fourth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 828 may be performed in embodiments to provide time to allow the reagent to coat portions of the bioreactor. For example, when the bioreactor comprises hollow fibers, step 828 may be performed to allow the reagent time to coat interior surfaces of the hollow fibers.

Flow 800 passes to optional step 832, where fluid with the reagent is circulated at a fifth flow rate, which may be less than the fourth flow rate. In embodiments, the fifth flow rate may be less than about 200 ml/min, less than about 150 ml/min, or even less than about 100 ml/min. In other embodiments, the fifth circulation rate may be greater than about 25 ml/min, greater than about 50 ml/min, or even greater than about 75 ml/min. In one embodiment, the fifth circulation flow rate is between about 25 ml/min and about 150 ml/min, such as about 100 ml/min.

Optional step 832 may be performed for a fifth predetermined period of time. In one specific example, the fifth period of time may be about 4 minutes, about 8 minutes, about 12 minutes, or even about 16 minutes. In other embodiments, the fifth predetermined period of time may be less than about 20 minutes, less than about 15 minutes, less than about 10 minutes, or even less than about 5 minutes. In some embodiments, the fifth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 832 may be performed in embodiments to provide time to allow the reagent to coat portions of the bioreactor. For example, when the bioreactor comprises hollow fibers, step 832 may be performed to allow the reagent time to coat interior surfaces of the hollow fibers.

Flow 800 passes to optional step 836, where fluid with the reagent is circulated at a sixth flow rate, which may be less than the fifth flow rate. In embodiments, the sixth flow rate may be less than about 100 ml/min, less than about 50 ml/min, or even less than about 25 ml/min. In other embodiments, the sixth circulation rate may be greater than about 5 ml/min, greater than about 10 ml/min, or even greater than about 15 ml/min. In one embodiment, the sixth circulation flow rate is between about 25 ml/min and about 100 ml/min, such as about 50 ml/min.

Optional step 836 may be performed for a sixth predetermined period of time. In one specific example, the sixth period of time may be about 4 minutes, about 8 minutes, about 12 minutes, or even about 16 minutes. In other embodiments, the sixth predetermined period of time may be less than about 20 minutes, less than about 15 minutes, less than about 10 minutes, or even less than about 5 minutes. In some embodiments, the sixth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 836 may be performed in embodiments to provide time to allow the reagent to coat portions of the bioreactor. For example, when the bioreactor comprises hollow fibers, step 836 may be performed to allow the reagent time to coat interior surfaces of the hollow fibers (e.g., the lumen).

Flow 800 passes to optional step 840, where fluid with the reagent is circulated at a seventh flow rate, which may be less than the sixth flow rate. In embodiments, the seventh flow rate may be less than about 100 ml/min, less than about 50 ml/min, or even less than about 25 ml/min. In other embodiments, the seventh circulation rate may be greater than about 10 ml/min, greater than about 15 ml/min, or even greater than about 20 ml/min. In one embodiment, the seventh circulation flow rate is between about 10 ml/min and about 50 ml/min, such as about 25 ml/min.

Optional step 840 may be performed for a seventh predetermined period of time. In one specific example, the seventh period of time may be about 4 minutes, about 8 minutes, about 12 minutes, or even about 16 minutes. In other embodiments, the sixth predetermined period of time may be less than about 20 minutes, less than about 15 minutes, less than about 10 minutes, or even less than about 5 minutes. In some embodiments, the sixth predetermined period of time may be greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or even greater than about 20 minutes. Step 840 may be performed in embodiments to provide time to allow the reagent to coat portions of the bioreactor. For example, when the bioreactor comprises hollow fibers, step 840 may be performed to allow the reagent time to coat interior surfaces of the hollow fibers.

Flow 800 then passes to optional step 844, where a second fluid, that may not include the reagent, or have a lower concentration of the reagent, may be circulated through the bioreactor. In embodiments, step 844 may be performed to wash any remaining reagent that has not coated a surface of the bioreactor out of the bioreactor and CES. As noted above, flow 800 may be part of a larger process such as a process for growing and harvesting cells in a cell expansion system, such as flow 700. Therefore, in embodiments, step 844 may be implemented as part of steps performed in the larger process, such as step 710 (FIG. 7). Flow 800 then ends at 848.

Figure 9:
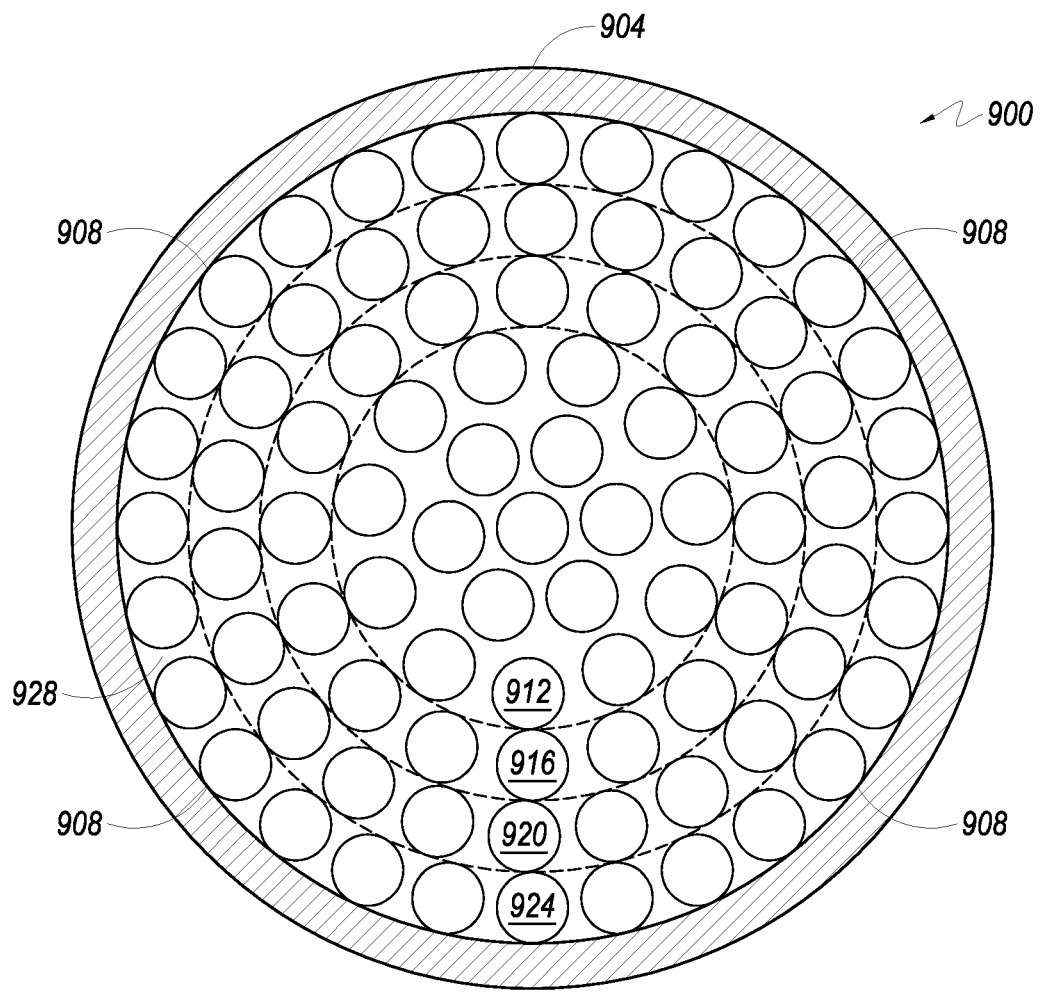
FIG. 9 illustrates a cross section of a bioreactor showing a plurality of hollow fibers and zones of hollow fibers through which liquid containing a reagent may circulate at different flow rates.

Referring now to FIG. 9, a cross section 900 (perpendicular to a central axis) of a bioreactor (e.g., bioreactor 100, 300, 501, and/or 601) is shown. The cross section 900 illustrates a plurality of hollow fibers 908 which may be within a housing 904. The cross section 900 is taken from one end of a bioreactor and illustrates, in addition to the hollow fibers 908 a matrix material 928 (which may be referred to above as potting material) that holds the hollow fibers 908 together.

Also shown in FIG. 9 are zones 912, 916, 920 and 924. These zones represent fibers that may have fluid circulating through them at different flow rates. Without being bound by theory, it is believed that circulation at relatively high flow rates, such as rates that may be used in circulation steps 816 and/or 820 (FIG. 8) may primarily flow through fibers in zone 912. It is believed that the higher flow rates do not allow fluid to disperse enough to flow evenly into the hollow fibers in the outer zones. As the flow rate is reduced, such as in steps 824, 828, 832, 836, 840, 844, and 848 it is believed that the fluid may disperse into hollow fibers in outer zones, such as 916, 920 and 924.

It is believed that having steps 816, 820, 824, 828, 832, 836, and 840 circulate at different flow rates, allows the fluid to flow through more of the hollow fibers 808 than if just a single flow rate would be used. In one embodiment of a process that follows flow chart 800, at steps 816 and 820, at the first flow rate and second flow rate respectively (described above), fluid may flow mainly through the hollow fibers in zone 912. At steps 824 and 828, the third flow rate and fourth flow rates respectively (described above), fluid may flow mainly through the hollow fibers in zones 912 and 916.

At steps 832 and 836, at the fifth flow rate and sixth flow rate respectively (described above), fluid may flow mainly through the hollow fibers in zone 912, 916, and 920 because the rate is slower and the fluid may disperse more. At step 840, at the seventh flow rate (described above), fluid may flow through the hollow fibers in zones 912, 916, 920, and 924 because the flow rate is yet slower and fluid may disperse even more. Thus, it is believed that fluid with the reagent may flow into more of the hollow fibers using a sequence of different flow rates, than if a single flow rate circulation is used.

Furthermore, it is also believed that the different flow rates may also affect the longitudinal distribution of the reagent along the bioreactor, e.g., along a hollow fiber. That is, a higher flow rate may allow the reagent to flow further along inside a hollow fiber. For example, at a higher flow rate, the reagent being carried by fluid may reach beyond half the length of the hollow fiber. At a lower flow rate, the reagent being carried by fluid may reach half the length of the hollow fiber. At even a lower flow rate, the reagent being carried by fluid may reach less than half the length of the hollow fiber. Accordingly, in some embodiments, it is believed that the use of different flow rates may provide some improvement in longitudinal distribution of the reagent along the length of the bioreactor, e.g., a hollow fiber.

As noted above, steps in flow 800 may be performed for predetermined periods of time. In embodiments, flow 800 may be designed to be performed within a period of time, e.g., 28 minutes, 56 minutes, 60 minutes, 90 minutes, and 120 minutes. For example, in embodiments, the predetermined period of times may be selected so that substantially all (or most) of the steps of flow 800 may be performed in less than 120 minutes, less than 90 minutes, such as less than 80 minutes, less than 70 minutes, less than 60 minutes, less than 50 minutes, less than 40 minutes, or even less than 30 minutes. In some embodiments, the steps of flow 800 may be performed in greater than 10 minutes, greater than 20 minutes, greater than 30 minutes, greater than 40 minutes, or greater than 50 minutes. In selecting the periods of time, embodiments provide for each period to be the same in duration. In other embodiments, each period of time may have a different duration. In yet other embodiments, some periods of time may have the same duration while others have different durations. These are merely some examples and flow 800 is not necessarily limited to being performed during any specific duration.

In one specific embodiment, flow 800 may provide for performing each of steps 816 through 840 in less than 30 minutes. As one example, each of the steps may be performed for 4 minutes resulting in a 28 minute coating process. As another example, each of steps 816 through 840 may be performed for 8 minutes resulting in a 56 minute coating process. These are merely some non-limiting examples.

Referring now to flow 1000, it starts at step 1004 and proceeds to step 1008 where fluid that includes a reagent may be introduced into a cell expansion system and a bioreactor such as bioreactors 100, 501, and/or 601. In embodiments, step 1008 may be similar to step 808 and involve activating one or more pumps (554, 654) to introduce fluid with the reagent from a bag (546) or connection point (646) into a fluid flow path.

As part of introducing the fluid with the reagent into the cell expansion system, step 1008 may involve optional step 1012, where a wash fluid (e.g., PBS) may be used to chase reagent from parts of the CES into bioreactor 501, 601. For example, the wash fluid may flow through path 506, 606 to move any reagent left behind in an ARC, such as ARC 556/656. The wash fluid may chase any lingering reagent into the bioreactor and/or the IC loop associated with the bioreactor, e.g., 502/602.

Flow 1000 passes to step 1016 where fluid that includes a reagent may be circulated through a bioreactor such as bioreactors 100, 501, and/or 601. In embodiments, step 816 may involve activating one or more pumps to circulate fluid with the reagent through the bioreactor. For example, an IC circulation pump (e.g., 512 or 612) may be activated to circulate fluid through the IC side of a bioreactor at a first circulation flow rate. In at least one embodiment, fluid may pass through hollow fibers (e.g., the lumen). Step 1016 may involve circulating fluid at a first flow rate. The first flow rate may in embodiments be one of the first flow rates described above with respect to step 816 (FIG. 8). Step 1016 may be performed for a first predetermined period of time. The first period of time may, in some embodiments, be one of the first periods of time described above with respect to step 816 (FIG. 8).

In some embodiments, step 1016 may involve circulation in a specific direction. In other words, in some embodiments, step 1016 may involve activating a pump such as IC circulation pump (e.g., 512 or 612) in a specific direction, e.g., a counter clockwise or a clockwise direction. As one example, referring now to FIG. 6, step 1016 may involve activating pump 612 to circulate fluid through path 602 and bioreactor 601 in a counter clock wise direction. That is, fluid may enter through port 601A and exit through port 601B.

Flow 1000 passes to step 1020, where fluid with the reagent is circulated at a second flow rate. In embodiments, the second flow rate may be one of the second flow rates described above with respect to step 820 (FIG. 8). Step 1020 may be performed for a second predetermined period of time, which may be one of the second predetermined periods of time described above with respect to step 820 (FIG. 8).

In some embodiments, step 1020 may involve circulation in a specific direction, such as a second direction opposite the first direction. Step 1020 may involve activating a pump such as IC circulation pump (e.g., 512 or 612) in a direction, e.g., a counter clockwise or a clockwise, opposite the first direction. Continuing with the example above, step 1016 may involve activating pump 612 to circulate fluid through path 602 and bioreactor 601 in a counter clock wise direction. Step 1020 may involve activating pump 612 to circulate fluid through path 602 and bioreactor 601 in a clock wise direction. That is, fluid may enter through port 601B and exit through port 601A.

Flow 1000 then passes to optional step 1024, where fluid with the reagent is circulated at a third flow rate. In embodiments, the third flow rate may be one of the third flow rates described above with respect to step 824 (FIG. 8). Step 1024 may be performed for a third predetermined period of time, which may be one of the third predetermined periods of time described above with respect to step 824 (FIG. 8).

In some embodiments, optional step 1024 may involve circulation in a specific direction, such as the first direction. Step 1024 may involve activating a pump such as IC circulation pump (e.g., 512 or 612) in a direction, e.g., a counter clockwise or a clockwise. Continuing with the example above, step 1024 may involve activating pump 612 to circulate fluid through path 602 and bioreactor 601 in a counter clock wise direction. That is, fluid may enter through port 601A and exit through port 601B.

Flow 1000 then passes to optional step 1028, where fluid with the reagent is circulated at a fourth flow rate. In embodiments, the fourth flow rate may be one of the fourth flow rates described above with respect to step 828 (FIG. 8). Step 1028 may be performed for a fourth predetermined period of time, which may be one of the fourth predetermined periods of time described above with respect to step 828 (FIG. 8).

In some embodiments, optional step 1028 may involve circulation in a specific direction, such as opposite the first direction. Step 1028 may involve activating a pump such as IC circulation pump (e.g., 512 or 612) in a direction, e.g., a counter clockwise or a clockwise. Continuing with the example above, step 1028 may involve activating pump 612 to circulate fluid through path 602 and bioreactor 601 in a clock wise direction. That is, fluid may enter through port 601B and exit through port 601A.

Flow 1000 then passes to optional step 1032, where fluid with the reagent is circulated at a fifth flow rate. In embodiments, the fifth flow rate may be one of the fifth flow rates described above with respect to step 832 (FIG. 8). Step 1032 may be performed for a fifth predetermined period of time, which may be one of the fifth predetermined periods of time described above with respect to step 832 (FIG. 8).

In some embodiments, step 1032 may involve circulation in a specific direction, such as the first direction. Step 1032 may involve activating a pump such as IC circulation pump (e.g., 512 or 612) in a direction, e.g., a counter clockwise or a clockwise. Continuing with the example above, step 1032 may involve activating pump 612 to circulate fluid through path 602 and bioreactor 601 in a counter clock wise direction. That is, fluid may enter through port 601A and exit through port 601B.

Flow 1000 then passes to optional step 1036, where fluid with the reagent is circulated at a sixth flow rate. In embodiments, the sixth flow rate may be one of the sixth flow rates described above with respect to step 836 (FIG. 8). Step 1036 may be performed for a sixth predetermined period of time, which may be one of the sixth predetermined periods of time described above with respect to step 836 (FIG. 8).

In some embodiments, step 1036 may involve circulation in a specific direction, such as opposite the first direction. Step 1036 may involve activating a pump such as IC circulation pump (e.g., 512 or 612) in a direction, e.g., a counter clockwise or a clockwise. Continuing with the example above, step 1036 may involve activating pump 612 to circulate fluid through path 602 and bioreactor 601 in a clock wise direction. That is, fluid may enter through port 601B and exit through port 601A.

Flow 1000 then passes to optional step 1040, where fluid with the reagent is circulated at a seventh flow rate. In embodiments, the seventh flow rate may be one of the seventh flow rates described above with respect to step 840 (FIG. 8). Step 1040 may be performed for a seventh predetermined period of time, which may be one of the seventh predetermined periods of time described above with respect to step 840 (FIG. 8).

In some embodiments, step 1040 may involve circulation in a specific direction, such as the first direction. Step 1040 may involve activating a pump such as IC circulation pump (e.g., 512 or 612) in a direction, e.g., a counter clockwise or a clockwise. Continuing with the example above, step 1040 may involve activating pump 612 to circulate fluid through path 602 and bioreactor 601 in a counter clock wise direction. That is, fluid may enter through port 601A and exit through port 601B.

Flow 1000 then passes to optional step 1044, where a second fluid, that may not include the reagent, or have a lower concentration of the reagent, may be circulated through the bioreactor. In embodiments, step 1044 may be performed to wash any remaining reagent that has not coated a surface of the bioreactor out of the bioreactor and CES. As noted above, flow 1000 may be part of a larger process such as a process for growing and harvesting cells in a cell expansion system, such as flow 700. Therefore, in embodiments, step 1044 may be implemented as part of steps performed in the larger process, such as step 710 (FIG. 7). Flow 1000 then ends at 1048.

Without being bound by theory, it is believed that having steps 1016, 1020, 1024, 1028, 1032, 1036, and 1040 circulate at different flow rates, allows the fluid to flow through more of the hollow fibers e.g., 908 (FIG. 9) than if just a single flow rate would be used. In one embodiment of a process that follows flow chart 1000, at steps 1016 and 1020 (at the first and second flow rates described above), fluid may flow mainly through the hollow fibers in zone 912. At steps 1024 and 1028 (at the third and fourth flow rates described above), fluid may flow mainly through the hollow fibers in zones 912 and 916.

At steps 1032 and 1036 (at the fifth and sixth flow rates described above), fluid may flow mainly through the hollow fibers in zone 912, 916, and 920 because the rate is slower and the fluid may disperse more. At step 1040 (at the seventh flow rates described above), fluid may flow through the hollow fibers in zones 912, 916, 920, and 924 because the flow rate is yet slower and fluid may disperse even more. Thus, it is believe that fluid with the reagent may flow into more of the hollow fibers using a sequence of different flow rates, than if a single flow rate circulation is used.

As noted above, it is also believed that the different flow rates may also affect the longitudinal distribution of the reagent along the bioreactor, e.g., along a hollow fiber. That is, a higher flow rate may allow the reagent to flow further along inside a hollow fiber. For example, at a higher flow rate, the reagent being carried by fluid may reach beyond half the length of the hollow fiber. At a lower flow rate, the reagent being carried by fluid may reach half the length of the hollow fiber. At even a lower flow rate, the reagent being carried by fluid may reach less than half the length of the hollow fiber. Accordingly, in some embodiments, it is believed that the use of different flow rates may provide some improvement in longitudinal distribution of the reagent along the length of the bioreactor, e.g., a hollow fiber. Additionally, with the changing of directions provided for in flow 1000, the reagent may be distributed along the length of the hollow fibers from both sides of a hollow fiber. The combination of flow rate changes and changes in direction, may allow for more even distribution of the reagent along the length of a hollow fiber.

As noted above, steps in flow 1000 may be performed for predetermined periods of time. In embodiments, flow 1000 may be designed to be performed within a period of time, e.g., relatively quickly. For example, in embodiments, the predetermined period of times may be selected so that substantially all (or most) of the steps of flow 1000 may be performed in less than 90 minutes, such as less than 80 minutes, less than 70 minutes, less than 60 minutes, less than 50 minutes, less than 40 minutes, or even less than 30 minutes. In some embodiments, the steps of flow 800 may be performed in greater than 10 minutes, greater than 20 minutes, greater than 30 minutes, greater than 40 minutes, or greater than 50 minutes. These are merely some examples and flow 1000 is not necessarily limited to being performed in a specific duration.

In selecting the periods of time, embodiments provide for each period to be the same in duration. In other embodiments, each period of time may have a different duration. In yet other embodiments, some periods of time may have the same duration while others have different durations. These are some examples; however, the steps of flow 1000 are not necessarily limited to any specific duration.

In one specific embodiment, flow 1000 may provide for performing each of steps 1016 through 1040 in less than 30 minutes. As one example, each of the steps may be performed for 4 minutes resulting in a 28 minute coating process. As another example, each of steps 1016 through 1040 may be performed for 8 minutes resulting in a 56 minute coating process. These are merely some non-limiting examples.

Referring now to FIG. 11, flow 1100 starts at 1102 and passes to step 1104 where fluid that includes a reagent may be introduced into a cell expansion system and a bioreactor such as bioreactors 100, 501, and/or 601. In embodiments, step 1104 may involve activating one or more pumps (554, 654) to introduce fluid with the reagent from a bag (546) or connection point (646) into a fluid flow path.

As part of introducing the fluid with the reagent into the cell expansion system, step 1104 may involve optional step 1106 where fluid that includes a reagent may be introduced into a cell expansion system and a bioreactor such as bioreactors 100, 501, and/or 601. In embodiments, step 1106 may be similar to step 808 and involve activating one or more pumps (554, 654) to introduce fluid with the reagent from a bag (546) or connection point (646) into a fluid flow path.

Flow 1100 passes to step 1108 which may be performed to orient a bioreactor, e.g. bioreactor 100, 501, and/or 601, to an initial orientation. In embodiments, a bioreactor may already be oriented in an initial orientation, in which case step 1108 would not be performed. When performed, step 1108 may in some embodiments be performed by one or more rotation mechanisms that may include one or more motors, gears, connectors, shafts, etc. that rotate the bioreactor to a first orientation (see, e.g., FIG. 1C). In embodiments, the orientation may be an initial horizontal orientation.

Figure 12:
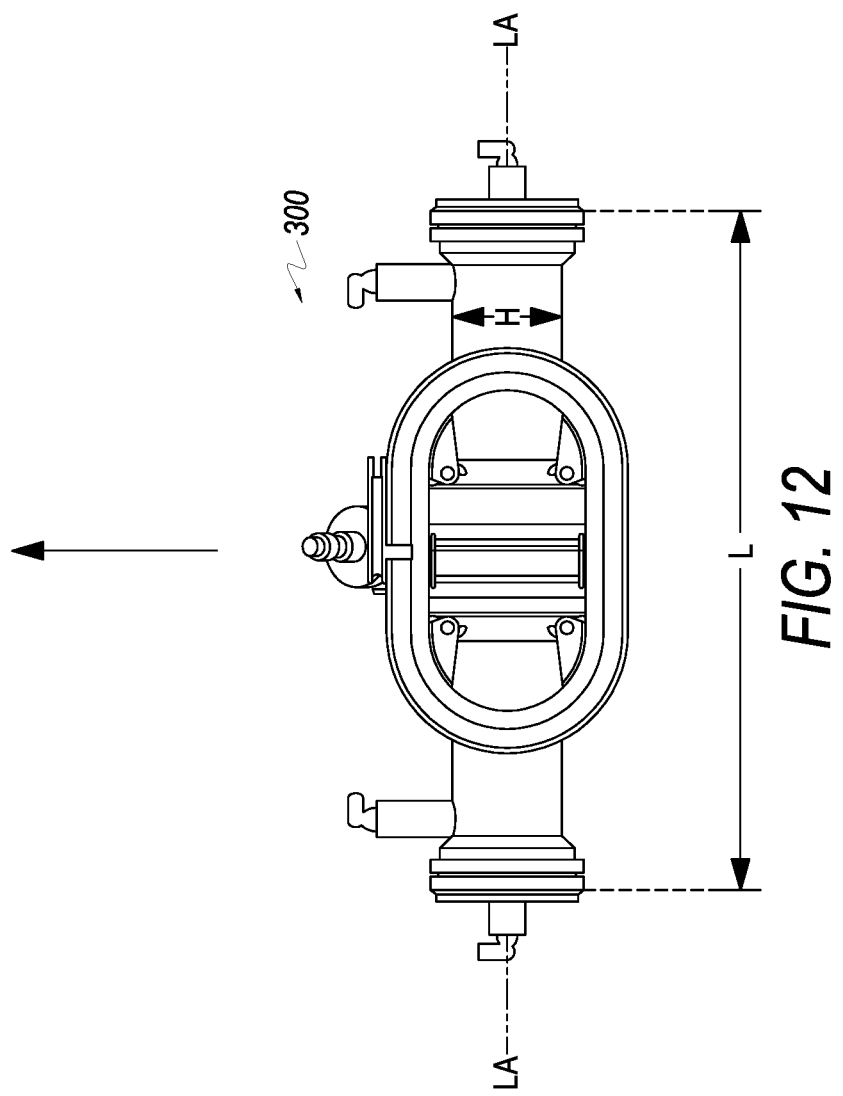
FIG. 12 illustrates a front elevation view of an embodiment of a bioreactor in a first orientation.
Figure 13:
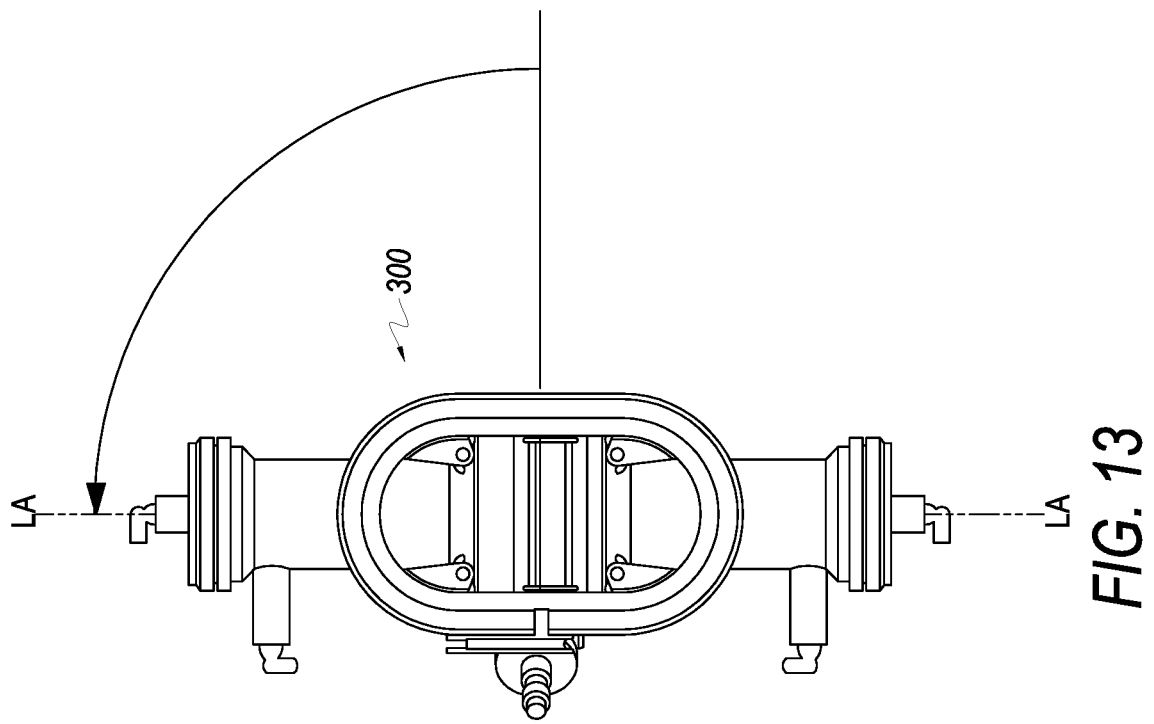
FIG. 13 illustrates a front elevation view of the bioreactor of FIG. 13, wherein the bioreactor is shown rotated about 90 degrees from the view of FIG. 13.
Figure 14:
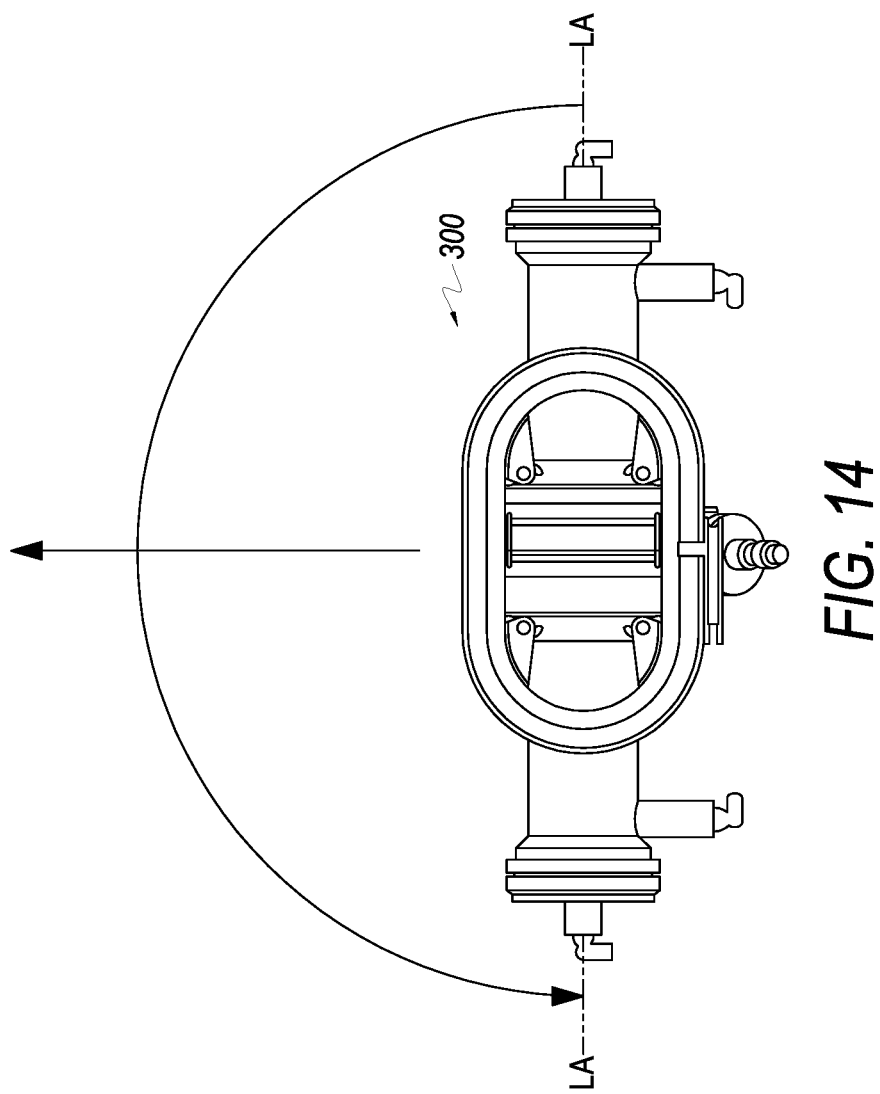
FIG. 14 is a front elevation view of the bioreactor of FIG. 12, wherein the bioreactor is shown rotated about 180 degrees from the view of FIG. 12.

Referring now to FIGS. 12-14, a bioreactor 300 (which in embodiments may be bioreactor 100, 501, and/or 601) is shown in different orientations. FIG. 12 illustrates the bioreactor 300 positioned in an initial orientation. As part of optional step 1108, bioreactor 300 may be oriented with its longitudinal axis LA-LA in a starting orientation, such as, for example, a first horizontal orientation as shown in FIG. 12.

Flow 1100 passes from optional step 1108 to step 1110 where fluid that includes a reagent may be circulated through a bioreactor such as bioreactors 100, 300, 501, and/or 601. In embodiments, step 1110 may involve activating one or more pumps to circulate fluid with the reagent through the bioreactor. For example, an IC circulation pump (e.g., 512 or 612) may be activated to circulate fluid through the IC side of a bioreactor at a first circulation flow rate.

In at least one embodiment, fluid may pass through hollow fibers (e.g., the lumen). Step 1110 may involve circulating fluid at a first flow rate. The first flow rate may in embodiments be one of the first flow rates described above with respect to step 816 (FIG. 8).

In other embodiments, fluid with the reagent may be circulated through the EC side of the bioreactor. Step 1110 may therefore, in embodiments, involve activating an EC circulation pump (e.g., 528 or 628) to circulate fluid through the EC side of bioreactor at a first circulation flow rate.

In embodiments, the reagent may be any protein, nutrient, or other material that is useful in creating conditions for expansion of cells. As described above, the reagent may be a protein that coats a surface in the bioreactor to which cell (e.g., adherent cells) may attach and grow. As one example, a glycoprotein (such as fibronectin, collagen, cryoprecipitate, etc.) may be the reagent that is circulated through a bioreactor, e.g., through the IC circuit of the bioreactor, to coat an inside surface of hollow fibers. The coating may promote the attachment of adherent cells that may later be added to the bioreactor and expanded in the bioreactor. This is merely one example and flow 1100 is not limited to this application.

In some embodiments, step 1110 may involve circulation in a specific direction. In other words, in some embodiments, step 1110 may involve activating a pump such as IC circulation pump (e.g., 512 or 612) in a first direction 1112, e.g., a counter clockwise or a clockwise direction. As one example, referring now to FIG. 6, step 1110 may involve activating pump 612 to circulate fluid through path 602 and bioreactor 601 in a counter clock wise direction. That is, fluid may enter through port 601A and exit through port 601B.

Flow 1100 passes from step 1110 to step 1114 where the bioreactor is maintained in the first orientation, e.g., a horizontal orientation (FIG. 12). Step 1114 may be performed in combination with step 1110. In embodiments, the first period of time may be one of the first periods of time described above with respect to step 816 (FIG. 8). Step 1114 may be performed in embodiments to provide time to allow the reagent to coat portions of the bioreactor. For example, when the bioreactor comprises hollow fibers, step 1114 may be performed to allow the reagent time to coat interior surfaces of the hollow fibers.

After step 1114, flow 1100 may pass to optional step 1116, where the bioreactor is rotated to a second orientation. In embodiments, the second orientation may be a horizontal orientation that is about 180 degrees from the original (e.g., first) orientation (e.g., FIG. 12). FIG. 13 illustrates bioreactor 300 rotated about 90 degrees from the orientation shown in FIG. 12, with FIG. 14 illustrating bioreactor 300 rotated about 180 degrees from the orientation shown in FIG. 12. In embodiments, step 1116 may be performed to rotate the bioreactor to an orientation shown in FIG. 14 (e.g., a second horizontal orientation). If step 1116 is not performed, flow would pass from step 1114 to step 1118. In these embodiments, the bioreactor may remain in the first orientation (e.g., first horizontal orientation as shown in FIG. 12).

Flow 1100 passes to step 1118, wherein fluid with the reagent is circulated at a second flow rate, which may be less than the first flow rate. In embodiments, the second flow rate may be one of the second flow rates described above with respect to step 820 (FIG. 8).

In some embodiments, step 1118 may involve circulation in a specific direction. In other words, in some embodiments, step 1118 may involve activating a pump such as IC circulation pump (e.g., 512 or 612) in a second direction 1120, e.g., a counter clockwise or a clockwise direction. Continuing with the example above, referring to FIG. 6, step 1120 may involve activating pump 612 to circulate fluid through path 602 and bioreactor 601 in a clock wise direction. That is, fluid may enter through port 601B and exit through port 601A.

Flow 1100 passes from step 1118 to optional step 1122 where the bioreactor is maintained in the second orientation, e.g., a second horizontal orientation (FIG. 14). Optional step 1122 may be performed in combination with optional step 1118. In embodiments, optional steps 1118 and 1122 may be performed for a second predetermined period of time. In embodiments, the second period of time may be one of the second periods of time described above with respect to step 820 (FIG. 8). Step 1122 may be performed in embodiments to provide time to allow the reagent to coat portions of the bioreactor. For example, when the bioreactor comprises hollow fibers, step 1122 may be performed to allow the reagent time to coat interior surfaces of the hollow fibers.

After optional step 1122, flow 1100 may pass to optional step 1124, where the bioreactor is rotated back to the first orientation. In embodiments, the first orientation may be a horizontal orientation that is about the same as the original (e.g., first) orientation (e.g., FIG. 12).

Flow 1100 passes from 1124 to optional step 1126, where fluid with the reagent is circulated at a third flow rate, which may be less than the second flow rate. In embodiments, the third flow rate may be one of the third flow rates described above with respect to step 824 (FIG. 8).

In some embodiments, optional step 1126 may involve circulation in a specific direction. In other words, in some embodiments, step 1126 may involve activating a pump such as IC circulation pump (e.g., 512 or 612) in the first direction 1128 e.g., a counter clockwise or a clockwise direction. Continuing with the example above, referring to FIG. 6, step 1126 may involve activating pump 612 to circulate fluid through path 602 and bioreactor 601 in a counter clock wise direction. That is, fluid may enter through port 601A and exit through port 601B.

Flow 1100 passes from optional step 1126 to optional step 1130 where the bioreactor is maintained in the first orientation, e.g., a first horizontal orientation (FIG. 12). Optional step 1130 may be performed in combination with optional step 1126. In embodiments, optional steps 1126 and 1130 may be performed for a third predetermined period of time. In embodiments, the third period of time may be one of the third periods of time described above with respect to step 824 (FIG. 8). Step 1130 may be performed in embodiments to provide time to allow the reagent to coat portions of the bioreactor. For example, when the bioreactor comprises hollow fibers, step 1130 may be performed to allow the reagent time to coat interior surfaces of the hollow fibers.

After optional step 1130, flow 1100 may pass to optional step 1132, where the bioreactor is rotated back to the second orientation. In embodiments, the second orientation may be a horizontal orientation that is about 180 degrees from the first orientation (e.g., FIG. 14).

Flow 1100 then passes to optional step 1134, where fluid with the reagent is circulated at a fourth flow rate, which may be less than the third flow rate. In embodiments, the fourth flow rate may be one of the fourth flow rates described above with respect to step 828 (FIG. 8).

In some embodiments, step 1134 may involve circulation in a specific direction. In other words, in some embodiments, step 1134 may involve activating a pump such as IC circulation pump (e.g., 512 or 612) in the second direction 1136 e.g., a counter clockwise or a clockwise direction. Continuing with the example above, referring to FIG. 6, step 1134 may involve activating pump 612 to circulate fluid through path 602 and bioreactor 601 in a clock wise direction. That is, fluid may enter through port 601B and exit through port 601A.

Flow 1100 passes from optional step 1134 to optional step 1138 where the bioreactor is maintained in the second orientation, e.g., a second horizontal orientation (FIG. 14). Optional step 1138 may be performed in combination with optional step 1134. In embodiments, optional steps 1134 and 1138 may be performed for a fourth predetermined period of time. In embodiments, the fourth period of time may be one of the fourth periods of time described above with respect to step 828 (FIG. 8). Step 1138 may be performed in embodiments to provide time to allow the reagent to coat portions of the bioreactor. For example, when the bioreactor comprises hollow fibers, step 1138 may be performed to allow the reagent time to coat interior surfaces of the hollow fibers.

After optional step 1138, flow 1100 may pass to optional step 1140, where the bioreactor is rotated back to the first orientation. In embodiments, the first orientation may be a horizontal orientation that is about the same as the original (e.g., first) orientation (e.g., FIG. 12).

Flow 1100 then passes to optional step 1142, wherein fluid with the reagent is circulated at a fifth flow rate, which may be less than the fourth flow rate. In embodiments, the fifth flow rate may be one of the fifth flow rates described above with respect to step 832 (FIG. 8).

In some embodiments, step 1142 may involve circulation in a specific direction. In other words, in some embodiments, step 1142 may involve activating a pump such as IC circulation pump (e.g., 512 or 612) in the first direction 1144 e.g., a counter clockwise or a clockwise direction. Continuing with the example above, referring to FIG. 6, step 1142 may involve activating pump 612 to circulate fluid through path 602 and bioreactor 601 in a counter clock wise direction. That is, fluid may enter through port 601A and exit through port 601B.

Flow 1100 passes from optional step 1142 to optional step 1146 where the bioreactor is maintained in the first orientation, e.g., a first horizontal orientation (FIG. 12). Optional step 1146 may be performed in combination with optional step 1142. In embodiments, optional steps 1142 and 1146 may be performed for a fifth predetermined period of time. In embodiments, the fifth period of time may be one of the fifth periods of time described above with respect to step 832 (FIG. 8). Step 1146 may be performed in embodiments to provide time to allow the reagent to coat portions of the bioreactor. For example, when the bioreactor comprises hollow fibers, step 1146 may be performed to allow the reagent time to coat interior surfaces of the hollow fibers.

After optional step 1146, flow 1100 may pass to optional step 1148, where the bioreactor is rotated back to the second orientation. In embodiments, the second orientation may be a horizontal orientation that is about 180 degrees from the original (e.g., first) orientation (e.g., FIG. 14).

Flow 1100 may then passes to optional step 1150, where fluid with the reagent is circulated at a sixth flow rate, which may be less than the fifth flow rate. In embodiments, the sixth flow rate may be one of the sixth flow rates described above with respect to step 836 (FIG. 8).

In some embodiments, optional step 1150 may involve circulation in a specific direction. In other words, in some embodiments, step 1150 may involve activating a pump such as IC circulation pump (e.g., 512 or 612) in the second direction 1152 e.g., a counter clockwise or a clockwise direction. Continuing with the example above, referring to FIG. 6, step 1150 may involve activating pump 612 to circulate fluid through path 602 and bioreactor 601 in a clock wise direction. That is, fluid may enter through port 601B and exit through port 601A.

Flow 1100 passes from optional step 1150 to optional step 1154 where the bioreactor is maintained in the second orientation, e.g., a second horizontal orientation (FIG. 14). Optional step 1154 may be performed in combination with optional step 1150. In embodiments, optional steps 1150 and 1154 may be performed for a sixth predetermined period of time. In embodiments, the sixth period of time may be one of the sixth periods of time described above with respect to step 836 (FIG. 8). Step 1154 may be performed in embodiments to provide time to allow the reagent to coat portions of the bioreactor. For example, when the bioreactor comprises hollow fibers, step 1154 may be performed to allow the reagent time to coat interior surfaces of the hollow fibers.

After optional step 1154, flow 1100 may pass to optional step 1156, where the bioreactor is rotated back to the first orientation. In embodiments, the first orientation may be a horizontal orientation that is substantially the same as the original (e.g., first) orientation (e.g., FIG. 12).

Flow 1100 may then pass to optional step 1158, where fluid with the reagent is circulated at a seventh flow rate, which may be less than the sixth flow rate. In embodiments, the seventh flow rate may be one of the seventh flow rates described above with respect to step 840 (FIG. 8).

In some embodiments, step 1158 may involve circulation in a specific direction. In other words, in some embodiments, step 1158 may involve activating a pump such as IC circulation pump (e.g., 512 or 612) in the first direction 1160 e.g., a counter clockwise or a clockwise direction. Continuing with the example above, referring to FIG. 6, step 1158 may involve activating pump 612 to circulate fluid through path 602 and bioreactor 601 in a counter clock wise direction. That is, fluid may enter through port 601A and exit through port 601B.

Flow 1100 passes from optional step 1158 to optional step 1162 where the bioreactor is maintained in the first orientation, e.g., a first horizontal orientation (FIG. 12). Optional step 1162 may be performed in combination with optional step 1158. In embodiments, optional steps 1158 and 1162 may be performed for a seventh predetermined period of time. In embodiments, the seventh period of time may be one of the seventh periods of time described above with respect to step 840 (FIG. 8). Step 1162 may be performed in embodiments to provide time to allow the reagent to coat portions of the bioreactor. For example, when the bioreactor comprises hollow fibers, step 1162 may be performed to allow the reagent time to coat interior surfaces of the hollow fibers.

Flow 1100 then passes to optional step 1164, where a second fluid, that may not include the reagent, or have a lower concentration of the reagent, may be circulated through the bioreactor. In embodiments, step 1164 may be performed to wash any remaining reagent that has not coated a surface of the bioreactor out of the bioreactor and CES. As noted above, flow 1100 may be part of a larger process such as a process for growing and harvesting cells in a cell expansion system, such as flow 700. Therefore, in embodiments, step 1164 may be implemented as part of steps performed in the larger process, such as step 710 (FIG. 7). Flow 1100 then ends at 1166.

Without being bound by theory, it is believed that having steps 1110, 1118, 1126, 1134, 1142, 1150, and 1158 circulate at different flow rates, allows the fluid to flow through more of the hollow fibers e.g., 908 (FIG. 9) than if just a single flow rate would be used. In one embodiment of a process that follows flow chart 1100, at steps 1110 and 1118 (at the first and second flow rates described above), fluid may flow mainly through the hollow fibers in zone 912. At steps 1126 and 1134 (at the third and fourth flow rates described above), fluid may flow mainly through the hollow fibers in zones 912 and 916.

At steps 1142 and 1150 (at the fifth and sixth flow rates described above), fluid may flow mainly through the hollow fibers in zone 912, 916, and 920 because the rate is slower and the fluid may disperse more. At step 1158 (at the seventh flow rates described above), fluid may flow through the hollow fibers in zones 912, 916, 920, and 924 because the flow rate is yet slower and fluid may disperse even more. Thus, it is believe that fluid with the reagent may flow into more of the hollow fibers using a sequence of different flow rates, than if a single flow rate circulation is used.

As noted above, it is also believed that the different flow rates may also affect the longitudinal distribution of the reagent along the bioreactor, e.g., along a hollow fiber. That is, a higher flow rate may allow the reagent to flow further along inside a hollow fiber. For example, at a higher flow rate, the reagent being carried by fluid may reach beyond half the length of the hollow fiber. At a lower flow rate, the reagent being carried by fluid may reach half the length of the hollow fiber. At even a lower flow rate, the reagent being carried by fluid may reach less than half the length of the hollow fiber. Accordingly, in some embodiments, it is believed that the use of different flow rates may provide some improvement in longitudinal distribution of the reagent along the length of the bioreactor, e.g., a hollow fiber. Additionally, with the changing of directions provided for in flow 1100, the reagent may be distributed along the length of the hollow fibers from both sides of a hollow fiber. The combination of flow rate changes and changes in direction, may allow for more even distribution of the reagent along the length of a hollow fiber.

Furthermore, flow 1100 provides for rotation of the bioreactor, as described above. It is also believed that rotation of the bioreactor, in addition to changes in direction and flow rates, provides a process where the reagent may be distributed/coated on hollow fibers more completely and/or uniformly. In other words, the rotation may utilize gravity to promote deposition of the coating reagent onto various portions of the growth surface, e.g., interior surface of a hollow fiber, which as described above is rotated.

As noted above, steps in flow 1100 may be performed for predetermined periods of time. In embodiments, flow 1100 may be designed to be performed within a period of time, e.g., 28 minutes, 56 minutes, 60 minutes, 90 minutes, and 120 minutes. For example, in embodiments, the predetermined period of times may be selected so that substantially all (or most) of the steps of flow 1100 may be performed in less than 120 minutes, less than 90 minutes, such as less than 80 minutes, less than 70 minutes, less than 60 minutes, less than 50 minutes, less than 40 minutes, or even less than 30 minutes. In some embodiments, flow 1100 may be performed in greater than 10 minutes, greater than 20 minutes, greater than 30 minutes, greater than 40 minutes, or greater than 50 minutes.

In selecting the periods of time, embodiments provide for each period to be the same in duration. In other embodiments, each period of time may have a different duration. In yet other embodiments, some periods of time may have the same duration while others have different durations. These are merely some examples and the steps of flow 1100 are not necessarily limited to any specific duration.

In one specific embodiment, flow 1100 may provide for performing each of steps 1110, 1118, 1126, 1134, 1142, 1150, and 1158 in less than 30 minutes. As one example, each of the steps may be performed for 4 minutes resulting in a 28 minute coating process. As another example, each of steps 1110, 1118, 1126, 1134, 1142, 1150, and 1158 may be performed for 8 minutes resulting in a 56 minute coating process. These are merely some non-limiting examples.

With respect to flows 700, 800, 1000, and 1100, illustrated in FIGS. 7, 8, 10, and 11, the operational steps depicted are offered for purposes of illustration and may be rearranged, combined into other steps, used in parallel with other steps, etc., according to embodiments of the present disclosure. Fewer or additional steps may be used in embodiments without departing from the spirit and scope of the present disclosure. Also, steps (and any sub-steps) may be performed automatically in some embodiments, such as by a processor executing pre-programmed tasks stored in memory, in which such steps are provided merely for illustrative purposes.

Also, it is noted that although flows 700, 800, 1000, and 1100, have been described above with various steps in particular order, the present invention is not limited thereto. In other embodiments, the various steps and sub-steps may be performed in a different order, in parallel, partially in the order shown in FIGS. 7, 8, 10, and 11 and/or in sequence. Also, the description above indicating that the step or sub-steps are performed by particular features or structures is not intended to limit the present invention. Rather, the description is provided merely for illustrative purposes. Other structures or features not described above may be used in other embodiments to perform one or more of the steps of flow 700. For example, some embodiments may combine features of flows 800, 1000, and 1100 with other coating processes, e.g., ultrafiltration, expedited coating processes, etc. Examples of other coating processes/steps that, in embodiments, may be utilized in combination with the embodiments described herein are described in U.S. patent application Ser. No. 15/616,635, entitled "METHODS AND SYSTEMS FOR COATING A CELL GROWTH SURFACE," filed Jun. 7, 2017, which claims priority to U.S. Provisional Patent Application No. 62/347,025, entitled "GROWTH SURFACE COATING," filed Jun. 7, 2016, both of which are hereby incorporated by reference in their entirety as if set forth herein in full.

Furthermore, flows, 700, 800, 1000, and 1100 may include some optional steps. However, those steps above that are not indicated as optional should not be considered as essential to the invention, but may be performed in some embodiments of the present invention and not in others.

Figure 15:
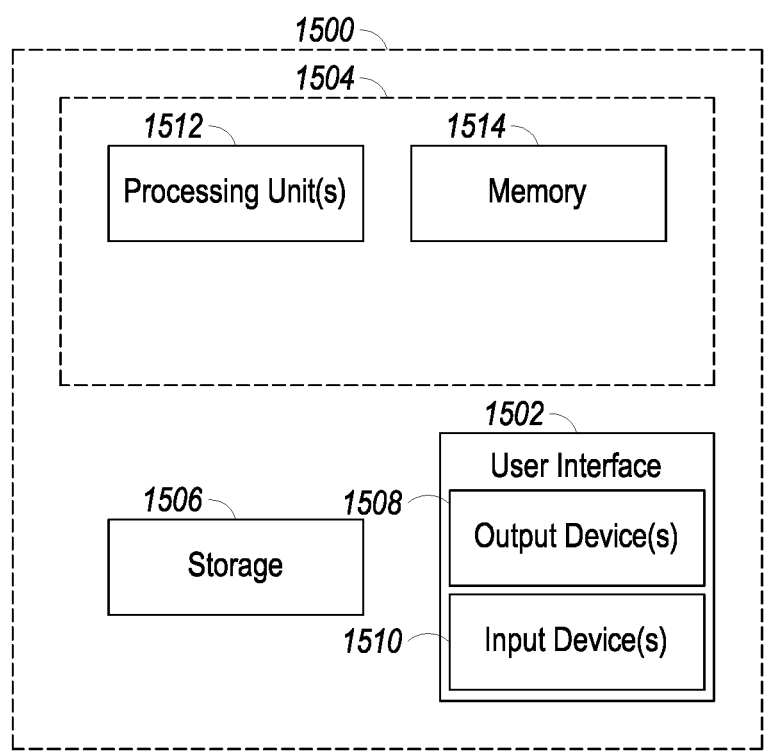
FIG. 15 illustrates components of a computing system that may be used to implement embodiments.

FIG. 15 illustrates example components of a computing system 1500 upon which embodiments of the present disclosure may be implemented. Computing system 1500 may be used in embodiments, for example, where a cell expansion system uses a processor to execute tasks, such as custom tasks or pre-programmed tasks performed as part of processes, such as the process illustrated by flows 700, 800, 1000, and 1100 and described above.

The computing system 1500 may include a user interface 1502, a processing system 1504, and/or storage 1506. The user interface 1502 may include output device(s) 1508, and/or input device(s) 1510 as understood by a person of skill in the art. Output device(s) 1508 may include one or more touch screens, in which the touch screen may comprise a display area for providing one or more application windows. The touch screen may also be an input device 1510 that may receive and/or capture physical touch events from a user or operator, for example. The touch screen may comprise a liquid crystal display (LCD) having a capacitance structure that allows the processing system 1504 to deduce the location(s) of touch event(s), as understood by those of skill in the art. The processing system 1504 may then map the location of touch events to user interface (UI) elements rendered in predetermined locations of an application window. The touch screen may also receive touch events through one or more other electronic structures, according to embodiments. Other output devices 1508 may include a printer, speaker, etc. Other input devices 1510 may include a keyboard, other touch input devices, mouse, voice input device, etc., as understood by a person of skill in the art.

Processing system 1504 may include a processing unit 1512 and/or a memory 1514, according to embodiments of the present disclosure. The processing unit 1512 may be a general purpose processor operable to execute instructions stored in memory 1514. Processing unit 1512 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits, etc., as understood by a person of skill in the art.

The memory 1514 may include any short-term or long-term storage for data and/or processor executable instructions, according to embodiments. The memory 1514 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, etc., as understood by a person of skill in the art.

Storage 1506 may be any long-term data storage device or component. Storage 1506 may include one or more of the systems described in conjunction with the memory 1514, according to embodiments. The storage 1506 may be permanent or removable. In embodiments, storage 1506 stores data generated or provided by the processing system 1504.

EXAMPLES

Results for some examples of protocols/methods/processes that may be used with a cell expansion system, such as CES 500 (FIG. 5) and/or CES 600 (FIG. 6), for example, that implement aspects of the embodiments shown in FIGS. 7, 8, 10, and 11 are described below. Although specific features may be described in the examples, such examples are provided merely for illustrative and descriptive purposes. For example, while examples may provide for the expansion of MSCs, other cell types may be used in other embodiments. The present embodiments are not limited to the examples provided herein.

It is noted that the example protocols/methods/processes are provided for illustrative purposes and are not intended to limit other embodiments, which may include different or additional steps, parameters, or other features. The example protocols/methods/processes, including the steps (and any sub-steps), may be performed automatically in some embodiments, such as by a processor executing custom tasks or pre-programmed tasks stored in memory. In other embodiments, the steps (and any sub-steps) may be performed through the combination of automated and manual execution of operations. In further embodiments, the steps (and any sub-steps) may be performed by an operator(s) or user(s) or through other manual means.

Example 1

Below is an example of a protocol that may be used for implementing embodiments of flows 800, 1000, and 1100 on CES systems such as CES 500, 600. Although specific settings are shown and described below, other embodiments may provide for different values.

Day: 0 Bulls-Eye Coat Bioreactor
Purpose: coats the bioreactor membrane with a reagent.
Step 1: loads a reagent into the IC loop until the bag is empty.
Step 2: chases the reagent from the ARC into the IC loop.
Step 3: coats the bioreactor using +UFR.
Before starting this task, the following preconditions may be satisfied:
Coating is preceded by system prime with RT PBS; and
Include 40 mL or more of air in the cell inlet bag.
Table 1 describes the bags of solution attached to each line when performing Coat Bioreactor. These solutions and corresponding volumes are based on some settings for this task.

TABLE 1

Solutions for Coat Bioreactor

| Bag | Solution in Bag | Volume (estimation) |
|---|---|---|
| Cell Inlet | None | N/A |
| Reagent | CPPT or Fibronectin | 6-25 mL CPPT in 100 mL total volume w/PBS or 5 mg Fibronectin in 100 mL total volume w/PBS |
| IC Media | None | N/A |
| Wash | PBS | 1 L |
| EC Media | None | N/A |

Coat Bioreactor pathway: Task>System Management>Coat Bioreactor

1 Enter the values for each setting for step 1 shown in Table 2.

TABLE 2

Step 1 for Coat Bioreactor

| Setting | Factory | Laboratory Modifications |
|---|---|---|
| IC Inlet | Reagent | |
| IC Inlet Rate | 10 mL/min | |
| IC Circulation Rate | 100 mL/min | |
| EC Inlet | None | |
| EC Inlet Rate | 0 mL/min | |
| EC Circulation Rate | 30 mL/min | |
| Outlet | EC Outlet | |
| Rocker Control | Stationary (0°) | |
| Stop Condition | Empty Bag | |

2 Enter the values for each setting for step 2 shown in Table 3.

TABLE 3

Step 2 Settings for Coat Bioreactor

| Setting | Factory | Laboratory Modifications |
|---|---|---|
| IC Inlet | Wash | |
| IC Inlet Rate | 10 mL/min | |
| IC Circulation Rate | 100 mL/min | |
| EC Inlet | None | |
| EC Inlet Rate | 0 mL/min | |
| EC Circulation Rate | 30 mL/min | |
| Outlet | EC Outlet | |
| Rocker Control | Stationary (0°) | |
| Stop Condition | IC Volume (22 mL) | |

3 Enter the values for each setting for step 3 shown in Table 4.

TABLE 4

Step 3 Settings for Coat Bioreactor

| Setting | Factory | Laboratory Modifications |
|---|---|---|
| IC Inlet | None | |
| IC Inlet Rate | 0 mL/min | |
| IC Circulation Rate | ~~20 mL/min~~ | −300 mL/min |
| EC Inlet | Wash | |
| EC Inlet Rate | 0.1 mL/min | |
| EC Circulation Rate | 30 mL/min | |
| Outlet | EC Outlet | |
| Rocker Control | Stationary (180°) | |
| Stop Condition | ~~Manual~~ | 4 min |

4 Enter the values for each setting for step 4 shown in Table 5.

TABLE 5

Step 4 Settings for Coat Bioreactor

| Setting | Factory | Laboratory Modifications |
|---|---|---|
| IC Inlet | None | |
| IC Inlet Rate | 0 mL/min | |
| IC Circulation Rate | 0 mL/min | 250 mL/min |
| EC Inlet | Wash | |
| EC Inlet Rate | 0.1 mL/min | |
| EC Circulation Rate | 30 mL/min | |
| Outlet | EC Outlet | |
| Rocker Control | Stationary (0°) | |
| Stop Condition | ~~Manual~~ | 4 min |

5 Enter the values for each setting for step 5 shown in Table 6.

TABLE 6

Step 5 Settings for Coat Bioreactor

| Setting | Factory | Laboratory Modifications |
|---|---|---|
| IC Inlet | None | |
| IC Inlet Rate | 0 mL/min | |
| IC Circulation Rate | ~~20 mL/min~~ | −200 mL/min |
| EC Inlet | Wash | |
| EC Inlet Rate | 0.1 mL/min | |
| EC Circulation Rate | 30 mL/min | |
| Outlet | EC Outlet | |
| Rocker Control | Stationary (180°) | |
| Stop Condition | ~~Manual~~ | 4 min |

6 Enter the values for each setting for step 6 shown in Table 7.

TABLE 7

| Step 6 Settings for Coat Bioreactor | | | |
|---|---|---|---|
| Setting | Factory | Laboratory | Modifications |
| IC Inlet | None | | |
| IC Inlet Rate | 0 mL/min | | |
| IC Circulation Rate | ~~20 mL/min~~ | | 150 mL/min |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | ~~Manual~~ | | 4 min |

7 Enter the values for each setting for step 7 shown in Table 8.

TABLE 8

| Step 7 Settings for Coat Bioreactor | | | |
|---|---|---|---|
| Setting | Factory | Laboratory | Modifications |
| IC Inlet | None | | |
| IC Inlet Rate | 0 mL/min | | |
| IC Circulation Rate | ~~20 mL/min~~ | | −100 mL/min |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (180°) | | |
| Stop Condition | ~~Manual~~ | | 4 min |

8 Enter the values for each setting for step 8 shown in Table 9.

TABLE 9

| Step 8 Settings for Coat Bioreactor | | | |
|---|---|---|---|
| Setting | Factory | Laboratory | Modifications |
| IC Inlet | None | | |
| IC Inlet Rate | 0 mL/min | | |
| IC Circulation Rate | ~~20 mL/min~~ | | 50 mL/min |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (0°) | | |
| Stop Condition | ~~Manual~~ | | 4 min |

9 Enter the values for each setting for step 9 shown in Table 10.

TABLE 10

| Step 9 Settings for Coat Bioreactor | | | |
|---|---|---|---|
| Setting | Factory | Laboratory | Modifications |
| IC Inlet | None | | |
| IC Inlet Rate | 0 mL/min | | |
| IC Circulation Rate | ~~20 mL/min~~ | | −25 mL/min |
| EC Inlet | Wash | | |
| EC Inlet Rate | 0.1 mL/min | | |
| EC Circulation Rate | 30 mL/min | | |
| Outlet | EC Outlet | | |
| Rocker Control | Stationary (180°) | | |
| Stop Condition | ~~Manual~~ | | 4 min |

Example 2

Figure 16A:
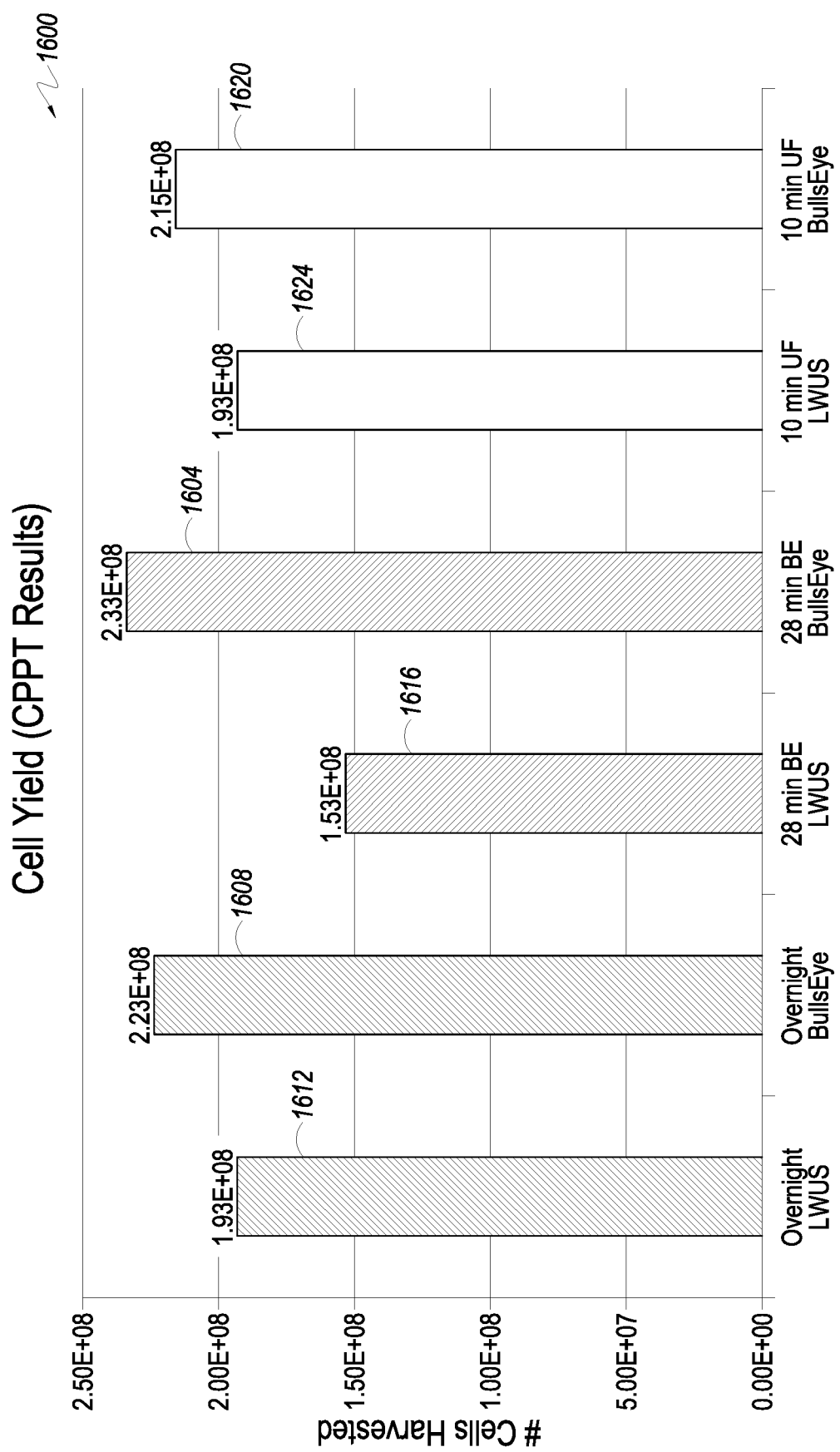
FIG. 16A illustrates example results of expanding cells using various coating and cell loading procedures in accordance with embodiments.
Figure 16B:
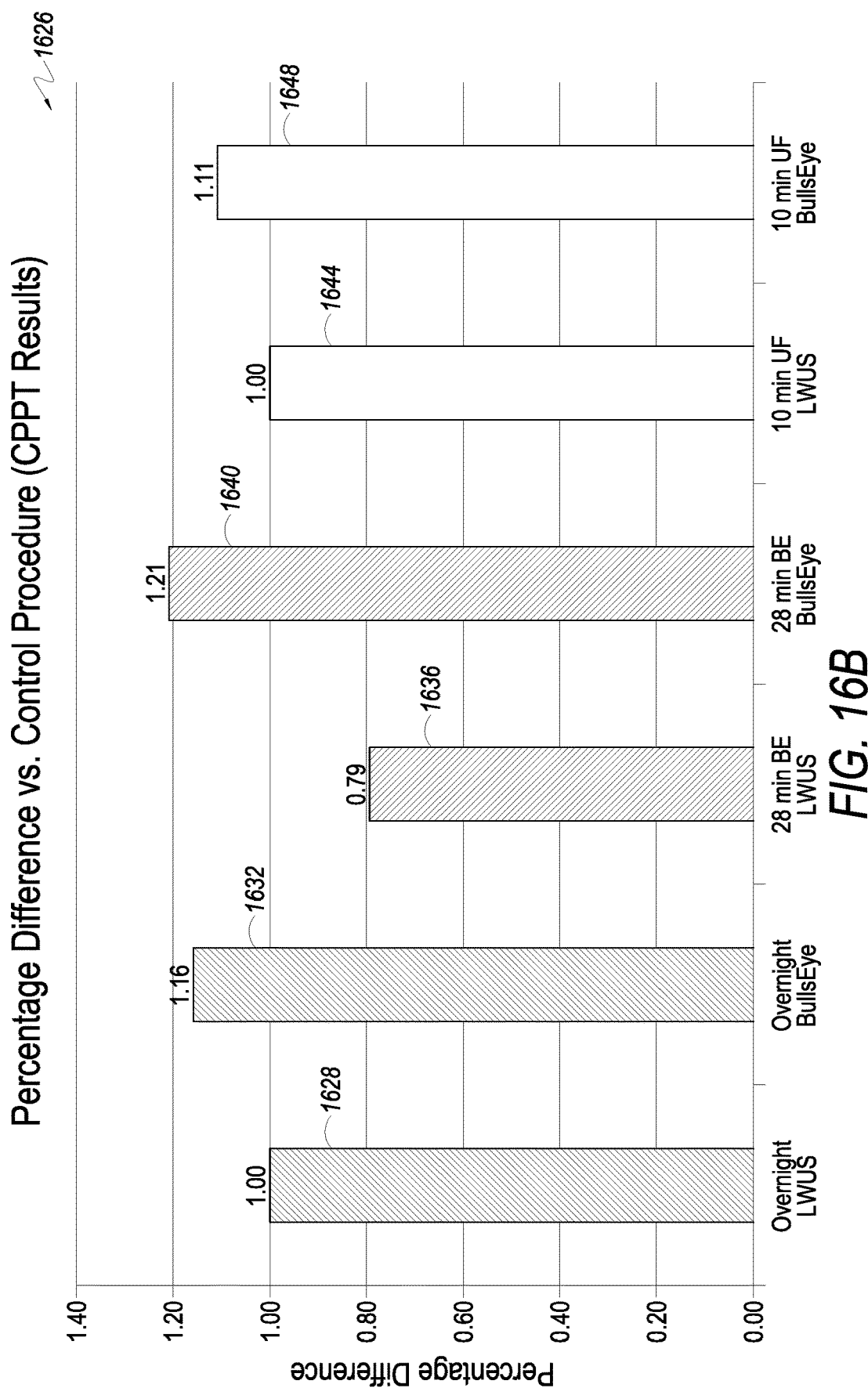
FIG. 16B depicts example results of expanding cells using various coating and cell loading procedures in accordance with embodiments.

Example results of expanding cells by coating a cell growth surface of a cell expansion system, such as CES 500 (FIG. 5) and/or CES 600 (FIG. 6), for example, with various coating procedures are illustrated in FIGS. 16A and 16B. For example, such cell growth surface coating and resulting cell expansion may use the Quantum® Cell Expansion System manufactured by Terumo BCT, Inc. in Lakewood, Colo. FIGS. 16A and 16B illustrate example results for coating a cell growth surface through a coating procedure with ultrafiltration, e.g., about 10-minute ultrafiltration coating procedure (10 min UF), versus coating using an overnight circulating coating procedure or a bulls-eye coating procedure, e.g., a 28-minute modified bulls-eye coating procedure (28 min BE). For example, a 10-minute positive ultrafiltration coating procedure may be used. In such procedures, 5 million MSCs may be loaded into the system, and 25 mL of a cryoprecipitate solution may be used for coating the cell growth surface of a hollow fiber bioreactor. The 28-minute bulls-eye coating time period used to coat the hollow fibers, e.g., fibers 812 (FIG. 8B), may be divided into seven (7) different time periods, each division being four (4) minutes long. During each 4-minute divisional time period, the circulation rate for the IC loop 502, 602 may be changed by adjusting the rate and/or direction of the circulation pump 512, 612. For example, the direction and/or circulation rate for the pump 512, 612 for each subsequent time division may be −300 mL/min, 250 mL/min, −200 mL/min, 150 mL/min, −100 mL/min, 50 mL/min, and −25 mL/min. The results from using these coating procedures with cryoprecipitate (CPPT) may be as shown in FIGS. 16A and 16B.

FIGS. 16A and 16B illustrate example results of using CPPT to coat the cell growth surface of a plurality of hollow fibers using various coating and cell loading procedures, and combinations thereof. As shown in graph 1600 of FIG. 16A, the 28-minute bulls-eye coating procedure (28 min BE) with bulls-eye cell loading procedure (BullsEye) may outperform the following procedures: the 28-minute bulls-eye coating procedure (28 min BE) with load with uniform suspension cell loading procedure (LWUS); the Overnight (o/n) coating procedure with load with uniform suspension cell loading procedure (LWUS); the Overnight coating procedure with bulls-eye cell loading procedure (BullsEye); the 10-minute ultrafiltration coating procedure (10 min UF) with load with uniform suspension cell loading procedure (LWUS); and the 10-minute ultrafiltration coating procedure (10 min UF) with bulls-eye cell loading procedure (BullsEye).

As shown in graph 1600 of FIG. 16A, the 28-minute bulls-eye coating procedure (28 min BE) procedure with bulls-eye cell loading procedure (BullsEye) may yield 2.33× $10^8$ cells 1604 while the Overnight coating procedure with bulls-eye cell loading procedure (BullsEye) may yield 2.23× $10^8$ cells 1608. The Overnight coating procedure with load with uniform suspension cell loading procedure (LWUS) may yield 1.93×$10^8$ cells 1612, while the 28-minute bulls-eye coating (28 min BE) procedure with load with uniform suspension cell loading procedure (LWUS) may yield 1.53× $10^8$ cells 1616. A 10-minute ultrafiltration procedure (10 min UF) with bulls-eye cell loading procedure (BullsEye) may result in 2.15×$10^8$ cells 1620, while a 10-minute ultrafiltration coating procedure (10 min UF) LWUS procedure may yield 1.93×$10^8$ cells 1624.

These example yields are compared in FIG. 16B. Graph 1626 of FIG. 16B illustrates a percentage difference versus control procedure using cryoprecipitate (CPPT) as a coating agent in various coating procedures and cell loading procedures, and combinations thereof. As shown in graph 1626 of FIG. 16B, compared to the Overnight coating procedure with load with uniform suspension cell loading procedure (LWUS) 1628, the Overnight coating procedure with bulls-eye cell loading procedure (BullsEye) may yield 16% 1632 more cells; the 28-minute bulls-eye coating (28 min BE) procedure with load with uniform suspension cell loading procedure (LWUS) may yield 21% 1636 fewer cells; the 28-minute bulls-eye coating procedure (28 min BE) with bulls-eye cell loading procedure (BullsEye) may yield 21% 1640 more cells; the 10-minute ultrafiltration coating procedure (10 min) with load with uniform suspension cell loading procedure (LWUS) may yield substantially the same number 1644 of cells; and the 10-minute ultrafiltration coating procedure (10 min) with bulls-eye cell loading procedure (BullsEye) may yield 11% 1648 more cells.

Example 3

Figure 17B:
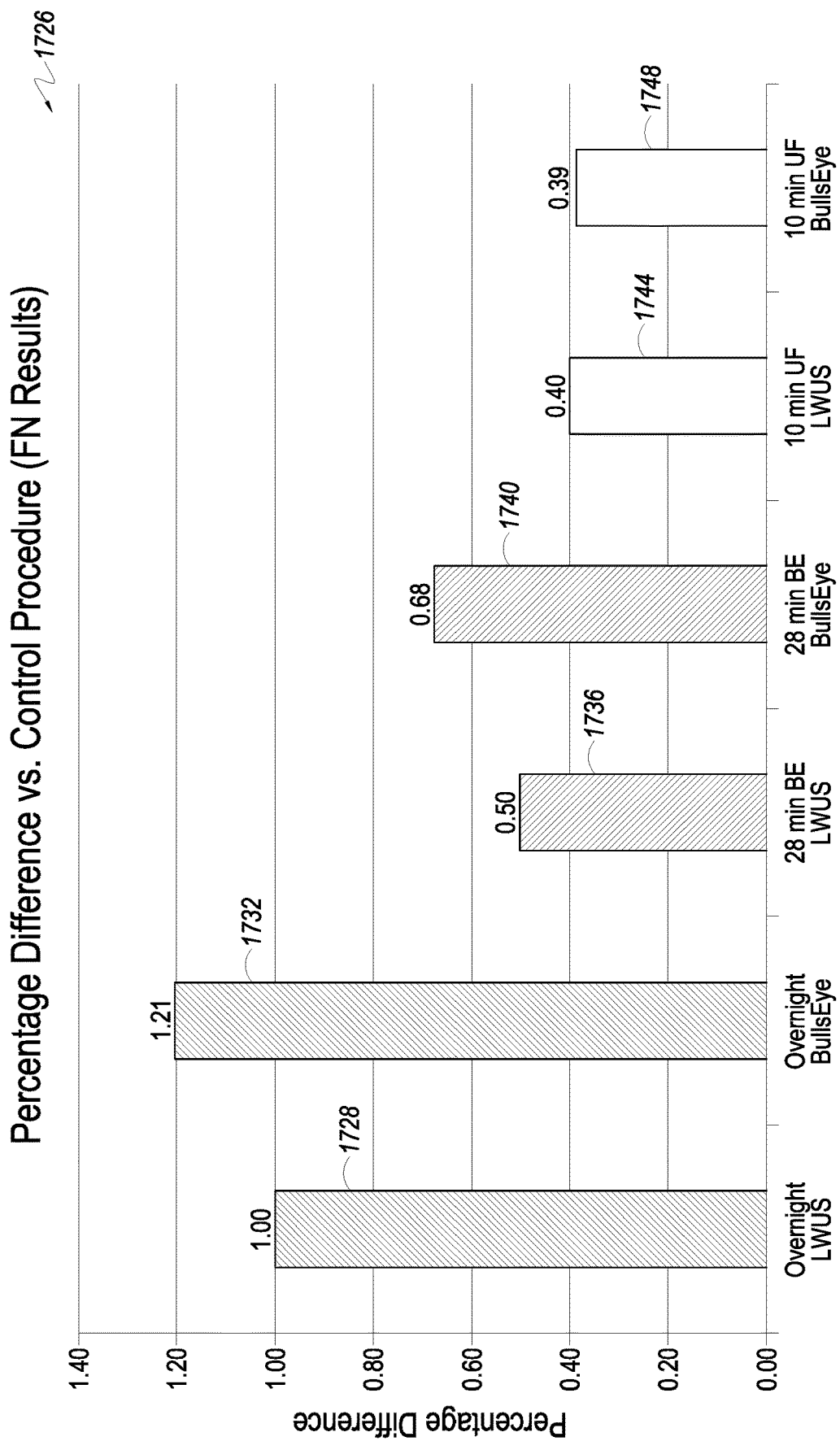
FIG. 17B depicts example results of expanding cells using various coating and cell loading procedures in accordance with embodiments.

Example results of expanding cells by coating a cell growth surface of a cell expansion system, such as CES 500 (FIG. 5) and/or CES 600 (FIG. 6), for example, with various coating procedures are illustrated in FIGS. 17A and 17B. For example, such cell growth surface coating and resulting cell expansion may use the Quantum® Cell Expansion System manufactured by Terumo BCT, Inc. in Lakewood, Colo. FIGS. 17A and 17B illustrate example results for coating a cell growth surface through a coating procedure with ultrafiltration, e.g., about 10-minute ultrafiltration coating procedure (10 min UF), versus coating using an overnight circulating coating procedure, or a bulls-eye coating (BE) procedure, e.g., a 28-minute modified bulls-eye coating procedure (28 min BE). For example, a 10-minute positive ultrafiltration coating procedure may be used. In such procedures, 5 million MSCs may be loaded into the system, and a 5 mg fibronectin (FN) solution may be used for coating the cell growth surface of a hollow fiber bioreactor. In an embodiment, such 5 mg FN solution may be circulated at 20 mL/minute. In the Quantum® System, such 5 mg FN solution may be circulated at 20 mL/minute in the 189 mL IC loop, according to an embodiment. The 28-minute bulls-eye coating time period used to coat the hollow fibers, e.g., fibers 908 (FIG. 9), may be divided into seven (7) different time periods, each division being four (4) minutes long. During each 4-minute divisional time period, the circulation rate for the IC loop 502, 602 may be changed by adjusting the rate and/or direction of the circulation pump 512, 612. For example, the direction and/or circulation rate for the pump 512, 612 for each subsequent time division may be −300 mL/min, 250 mL/min, −200 mL/min, 150 mL/min, −100 mL/min, 50 mL/min, and −25 mL/min. The results from using these coating procedures with fibronectin (FN) may be as shown in FIGS. 17A and 17B.

FIGS. 17A and 17B illustrate example results of using FN to coat the cell growth surface of a plurality of hollow fibers using various coating and cell loading procedures, and combinations thereof.

The Overnight coating procedure with bulls-eye cell loading procedure (BullsEye) may outperform the following: the Overnight coating procedure with load with uniform suspension cell loading procedure (LWUS); the 28-minute bulls-eye coating (28 min BE) procedure with load with uniform suspension cell loading procedure (LWUS); the 28-minute bulls-eye coating (28 min BE) procedure with bulls-eye cell loading procedure (BullsEye); the 10-minute ultrafiltration coating procedure (10 min UF) with load with uniform suspension cell loading procedure (LWUS); and the 10-minute ultrafiltration coating procedure (10 min UF) with bulls-eye cell loading procedure (BullsEye). As shown in graph 1700 of FIG. 17A, the 28-minute bulls-eye coating procedure (28 min BE) with bulls-eye cell loading procedure (BullsEye) may yield $1.29 \times 10^8$ cells 1704, while the Overnight coating procedure with bulls-eye cell loading procedure (BullsEye) may yield $2.30 \times 10^8$ cells 1708. The Overnight coating procedure with load with uniform suspension cell loading procedure (LWUS) may yield $1 \times 10^8$ cells 1712, while the 28-minute bulls-eye coating procedure (28 min BE) with load with uniform suspension cell loading procedure (LWUS) may yield $9.57 \times 10^7$ cells 1716. A 10-minute ultrafiltration coating procedure (10 min UF) with a bulls-eye cell loading procedure (BullsEye) may result in $7.34 \times 10^7$ cells 1720, while a 10-minute ultrafiltration procedure (10 min UF) with load with uniform suspension cell loading procedure (LWUS) may yield $7.54 \times 10^7$ cells 1724.

These example yields are compared in FIG. 17B. Graph 1726 of FIG. 17B illustrates a percentage difference versus control procedure using fibronectin (FN) as a coating agent using in various coating procedures and cell loading procedures, and combinations thereof. As shown in graph 1726 of FIG. 17B, compared to the Overnight coating procedure with load with uniform suspension cell loading procedure (LWUS) 1728, the Overnight coating procedure with bulls-eye cell loading procedure (BullsEye) may yield 21% 1732 more cells; the 28-minute bulls-eye coating procedure with load with uniform suspension cell loading procedure (LWUS) may yield 50% 1736 fewer cells; the 28-minute bulls-eye coating procedure (28 min BE) with bulls-eye cell loading procedure (BullsEye) may yield 32% 1740 fewer cells; the 10-minute ultrafiltration coating procedure (10 min) with load with uniform suspension cell loading procedure (LWUS) may yield 60% 1744 fewer cells; and the 10-minute ultrafiltration coating procedure (10 min) with bulls-eye cell loading procedure (BullsEye) may yield 61% 1748 fewer cells.

Example 4

Figure 18A:
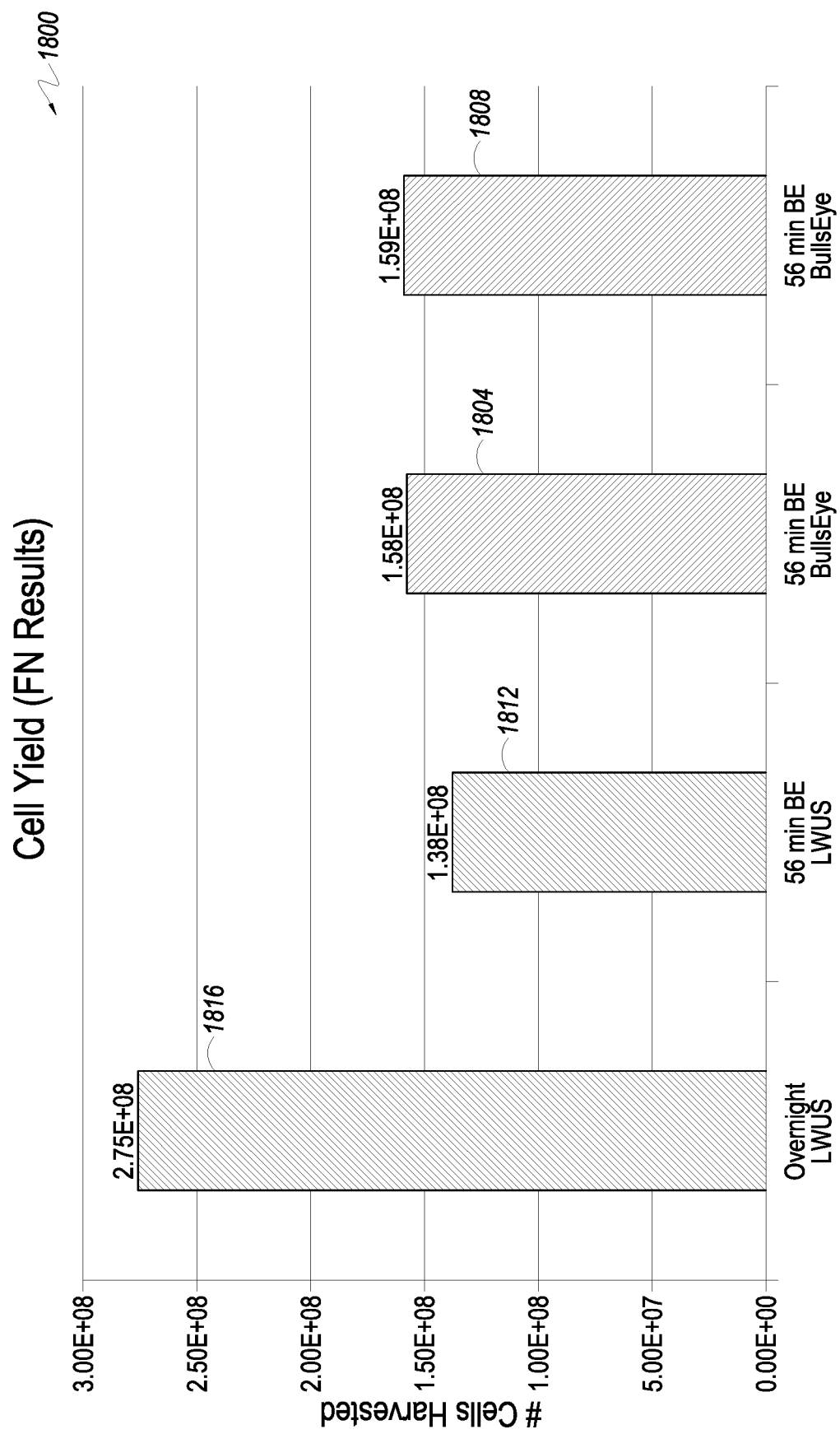
FIG. 18A illustrates example results of expanding cells using various coating and cell loading procedures in accordance with embodiments.

Example results of expanding cells by coating a cell growth surface of a cell expansion system, such as CES 500 (FIG. 5) and/or CES 600 (FIG. 6), for example, with various coating procedures are illustrated in FIGS. 18A and 18B. For example, such cell growth surface coating and resulting cell expansion may use the Quantum® Cell Expansion System manufactured by Terumo BCT, Inc. in Lakewood, Colo. FIGS. 18A and 18B illustrate example results for coating a cell growth surface through a coating procedure with coating using an overnight circulating coating procedure versus a bulls-eye coating procedure, e.g., a 56-minute modified bulls-eye coating procedure (56 min BE). In such procedures, 5 million MSCs may be loaded into the system, and a 5 mg fibronectin (FN) solution may be used for coating the cell growth surface of a hollow fiber bioreactor. In an embodiment, such 5 mg FN solution may be circulated at 20 mL/minute. In the Quantum® System, such 5 mg FN solution may be circulated at 20 mL/minute in the 189 mL IC loop, according to an embodiment. The 56-minute bulls-eye coating (56 min BE) time period used to coat the hollow fibers, e.g., fibers 908 (FIG. 9), may be divided into seven (7) different time periods, each division being minutes (8) minutes long. During each 8-minute divisional time period, the circulation rate for the IC loop 502, 602 may be changed by adjusting the rate and/or direction of the circulation pump 512, 612. For example, the direction and/or circulation rate for the pump 512, 612 for each subsequent time division may be −300 mL/min, 250 mL/min, −200 mL/min, 150 mL/min, −100 mL/min, 50 mL/min, and −25 mL/min. The results from using these coating procedures with fibronectin (FN) may be as shown in FIGS. 18A and 18B.

FIGS. 18A and 18B illustrate example results of using FN to coat the cell growth surface of a plurality of hollow fibers using various coating and cell loading procedures, and combinations thereof.

The Overnight coating procedure with uniform suspension cell loading procedure (LWUS) may outperform the following: the 56-minute bulls-eye coating (56 min BE) procedure with uniform suspension cell loading procedure (LWUS) and the 56-minute bulls-eye coating procedure (56 min BE) with BullsEye loading procedure. As shown in graph 1800 of FIG. 18A, the 56-minute bulls-eye coating procedure (56 min BE) with bulls-eye cell loading procedure (BullsEye) may yield $1.58 \times 10^8$ cells 1804 in a first run and $1.59 \times 10^8$ cells 1808 in a second run. The 56-minute bulls-eye coating procedure (56 min BE) with uniform suspension cell loading (LWUS) may yield $1.38 \times 10^8$ cells 1812. The Overnight coating procedure with uniform suspension cell loading procedure (LWUS) may yield $2.75 \times 10^8$ cells 1816.

These example yields are compared in FIG. 18B. Graph 1820 of FIG. 18B illustrates a percentage difference versus control procedure using fibronectin (FN) as a coating agent using various coating procedures and cell loading procedures, and combinations thereof. As shown in graph 1820 of FIG. 18B, compared to the Overnight coating procedure with load with uniform suspension cell loading procedure (LWUS) 1824, the 56-minute bulls-eye coating procedure (56 min BE) with uniform suspension cell loading procedure (LWUS) may yield 50% 1828 fewer cells; the 56-minute bulls-eye coating procedure (56 min BE) with bulls-eye cell loading procedure (BullsEye) may yield 43% 1832 fewer cells in a first run, and 42% 1836 fewer cells in a second run.

It will be apparent to those skilled in the art that various modifications and variations can be made to the methods and structure of the present invention without departing from its scope. Thus it should be understood that the present invention is not be limited to the specific examples given. Rather, the present invention is intended to cover modifications and variations within the scope of the following claims and their equivalents.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" can mean A alone, B alone, C alone, A and B together, A and C together, B and C together, or A, B and C together.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the present invention.

What is claimed is:

1. A method of coating a bioreactor, the method comprising:
    circulating a first fluid at a first flow rate through a bioreactor of a cell expansion system, wherein the first fluid comprises a glycoprotein;
    while circulating, maintaining the bioreactor in a first orientation for a first period of time to allow at least a first portion of the glycoprotein to coat the bioreactor;
    after the first period of time, circulating the first fluid at a second flow rate slower than the first flow rate through the bioreactor of the cell expansion system for a second period of time to allow a second portion of the glycoprotein to coat the bioreactor; and
    circulating a second fluid through the bioreactor to remove a portion of the glycoprotein not coated on the bioreactor.

2. The method of claim 1, wherein the circulating the first fluid at a second flow rate is in a direction opposite a direction of the circulating the first fluid at the first flow rate.

3. The method of claim 2, further comprising rotating the bioreactor to a second orientation that is about 180 degrees from the first orientation after the first period of time and before the circulating the first fluid at the second flow rate.

4. The method of claim 3, after the second predetermined period of time, circulating the first fluid at a third flow rate slower than the second flow rate through the bioreactor of the cell expansion system for a third period of time to allow a third portion of the glycoprotein to coat the bioreactor.

5. The method of claim 4, wherein the circulating the first fluid at the third flow rate is in the same direction as the direction of the circulating the first fluid at the first flow rate.

6. The method of claim 5, further comprising rotating the bioreactor back to the first orientation after the second period of time and before the circulating the first fluid at the third flow rate.

7. The method of claim 6, after the third period of time, circulating the first fluid at a forth flow rate slower than the third flow rate through the bioreactor of the cell expansion system for a fourth period of time to allow a forth portion of the glycoprotein to coat the bioreactor.

8. The method of claim 7, wherein the circulating the first fluid at the fourth flow rate is in the opposite direction as the direction of the circulating the first fluid at the first flow rate.

9. The method of claim 8, further comprising rotating the bioreactor back to the second orientation after the third period of time and before the circulating the first fluid at the fourth flow rate.

10. The method of claim 9, after the fourth period of time, circulating the first fluid at a fifth flow rate slower than the fourth flow rate through the bioreactor of the cell expansion system for a fifth period of time to allow a fifth portion of the glycoprotein to coat the bioreactor.

11. The method of claim 10, wherein the circulating the first fluid at the fifth flow rate is in the same direction as the direction of the circulating the first fluid at the first flow rate.

12. The method of claim 11, further comprising rotating the bioreactor back to the first orientation after the fourth period of time and before the circulating the first fluid at the fifth flow rate.

13. The method of claim 12, after the fifth period of time, circulating the first fluid at a sixth flow rate slower than the fifth flow rate through the bioreactor of the cell expansion system for a sixth period of time to allow a sixth portion of the glycoprotein to coat the bioreactor.

14. The method of claim 13, wherein the circulating the first fluid at the sixth flow rate is in the opposite direction as the direction of the circulating the first fluid at the first flow rate.

15. The method of claim 14, further comprising rotating the bioreactor back to the second orientation after the fifth period of time and before the circulating the first fluid at the sixth flow rate.

16. The method of claim 15, after the sixth period of time, circulating the first fluid at a seventh flow rate slower than the sixth flow rate through the bioreactor of the cell expansion system for a seventh period of time to allow a seventh portion of the glycoprotein to coat the bioreactor.

17. The method of claim 16, wherein the circulating the first fluid at the seventh flow rate is in the same direction as the direction of the circulating the first fluid at the first flow rate.

18. The method of claim 17, further comprising rotating the bioreactor back to the first orientation after the sixth period of time and before the circulating the first fluid at the seventh flow rate.

19. The method of claim 18, wherein the method is completed in less than sixty minutes.

20. A method of coating a bioreactor, the method comprising:
    circulating a first fluid at a first flow rate through a bioreactor of a cell expansion system, wherein the first fluid comprises a glycoprotein;
    circulating the first fluid for a first period of time to allow at least a first portion of the glycoprotein to coat the bioreactor; and
    after the first period of time, circulating the first fluid at a second flow rate slower than the first flow rate through the bioreactor of the cell expansion system for a second period of time to allow a second portion of the glycoprotein to coat the bioreactor; and
    circulating a second fluid through the bioreactor to remove a third portion of the glycoprotein from the bioreactor.

21. The method of claim 20, wherein the circulating the first fluid at a second flow rate is in a direction opposite a direction of the circulating the first fluid at the first flow rate.

22. The method of claim 21, further comprising after the second predetermined period of time, circulating the first fluid at a third flow rate slower than the second flow rate through the bioreactor of the cell expansion system for a third period of time to allow a third portion of the glycoprotein to coat the bioreactor.

23. The method of claim 22, wherein the circulating the first fluid at the third flow rate is in the same direction as the direction of the circulating the first fluid at the first flow rate.

24. The method of claim 22, further comprising after the third period of time, circulating the first fluid at a fourth flow rate slower than the third flow rate through the bioreactor of the cell expansion system for a fourth period of time to allow a fourth portion of the glycoprotein to coat the bioreactor.

25. The method of claim 24, wherein the circulating the first fluid at the fourth flow rate is in the opposite direction as the direction of the circulating the first fluid at the first flow rate.

* * * * *